US012624084B2

(12) United States Patent
Hu et al.

(10) Patent No.: US 12,624,084 B2
(45) Date of Patent: May 12, 2026

(54) T CELL RECEPTOR RECOGNISING KRAS MUTATION AND ENCODING SEQUENCE THEREOF

(71) Applicant: XLIFESC, LTD., Guangdong (CN)

(72) Inventors: Jing Hu, Guangdong (CN); Hanli Sun, Guangdong (CN)

(73) Assignee: XLIFESC, LTD., Guangdong (CN)

( * ) Notice: Subject to any disclaimer, the term of this patent is extended or adjusted under 35 U.S.C. 154(b) by 1070 days.

(21) Appl. No.: 17/767,695

(22) PCT Filed: Oct. 10, 2020

(86) PCT No.: PCT/CN2020/120191
§ 371 (c)(1),
(2) Date: Apr. 8, 2022

(87) PCT Pub. No.: WO2021/068938
PCT Pub. Date: Apr. 15, 2021

(65) Prior Publication Data
US 2023/0159613 A1 May 25, 2023

(30) Foreign Application Priority Data
Oct. 10, 2019 (CN) .......................... 201910960523.3

(51) Int. Cl.
| | |
|---|---|
| *C07K 14/725* | (2006.01) |
| *A61K 38/00* | (2006.01) |
| *A61K 40/11* | (2025.01) |
| *A61K 40/32* | (2025.01) |
| *A61K 40/42* | (2025.01) |
| *A61K 47/68* | (2017.01) |
| *A61P 35/00* | (2006.01) |
| *C12N 5/0783* | (2010.01) |

(52) U.S. Cl.
CPC .......... *C07K 14/7051* (2013.01); *A61K 40/11* (2025.01); *A61K 40/32* (2025.01); *A61K 40/4253* (2025.01); *A61K 47/6811* (2017.08); *A61K 47/6849* (2017.08); *A61P 35/00* (2018.01); *C12N 5/0636* (2013.01); *A61K 38/00* (2013.01); *C12N 2501/2302* (2013.01); *C12N 2501/2307* (2013.01)

(58) Field of Classification Search
None
See application file for complete search history.

(56) References Cited

U.S. PATENT DOCUMENTS

| | | | |
|---|---|---|---|
| 2008/0292549 A1 | 11/2008 | Jakobsen et al. | |
| 2016/0130319 A1 | 5/2016 | Li | |
| 2017/0304421 A1 | 10/2017 | Wang et al. | |

FOREIGN PATENT DOCUMENTS

| | | |
|---|---|---|
| CN | 107223134 A | 9/2017 |
| CN | 108395479 A | 8/2018 |
| CN | 110272482 A | 9/2019 |
| JP | 2017536825 A | 12/2017 |
| WO | 2016085904 A1 | 6/2016 |
| WO | 2019112941 A1 | 6/2019 |

OTHER PUBLICATIONS

Janeway et al., Immunobiology, 9th Ed., Garland Science, pp. 153-169, (2017) (Year: 2017).*
ESA retrieved on Apr. 28, 2025 from <URL:www.esa.int/Science_Exploration/Space_Science/Herschel/How_many_stars_are_there_in_the_Universe> (Year: 2025).*
Garcia et al., Cell, vol. 122, 333-336, Aug. 12, 2005 (Year: 2005).*
Goyarts et al. Mol Immunol. Jul. 1998;35(10):593-607 (Year: 1998).*
UniProt.org. P01848 Trac_Human. Version History Jun. 20, 2018. Retrieved on Apr. 29, 2025 from <URL: https://www.uniprot.org/uniprotkb/P01848/history> (Year: 2018).*
Tunnacliffe et al. 1985. Proc Natl Acad Sci. 82:5068-5072 (Year: 1985).*
TRBC2*01 by UniProt.org. P0DSE2 TRBR1_Human. Publications reference #4. Retrieved on Apr. 29, 2025 from <URL: https://www.uniprot.org/uniprotkb/P0DSE2/publications> (Year: 2025).*
Liu et al. Sep. 2019. Acta Pharmaceutica Sinica B. 9(5):871-879 (Year: 2019).*
First Chinese Office Action of Chinese Application No. 201910960523.3, along with English Translation thereof (16 pages).
Liu et al., "T-Cell Transfer Immunological Therapy Targeting Mutant KRAS in Cancer", The Journal of Evidence-Based Medicine, Feb. 2017, 17(1): 37-41.
Pengfei, et al., "Kras Mutation in Tumorigenesis and Cancer Therapy", Chinese Journal of Cell Biology, 2018; 40(2): 159-170.
Veatch, et al., "Endogenous CD4+ T cells recognize neoantigens in lung cancer patients, including recurrent oncogenic KRAS and ERBB2 (Her2) driver mutations", Cancer Immunol Res., Jun. 2019; 7(6): 910-922.
Search Report in European Application No. 20875414.3 dated Oct. 17, 2023, 9 pages.
First Japanese Office Action of Japanese Application No. 2022-521508 dated Apr. 21, 2023, along with English Translation thereof (9 pages).
Wang, et al., "Identification of T-cell Receptors Targeting KRAS-Mutated Human Tumors", Cancer Immunol Res., Mar. 2016; 4(3): 204-214, 12 pages.
Cafri et al., "Memory T cells targeting oncogenic mutations detected in peripheral blood of epithelial cancer patients," Nature Communications, vol. 10, No. 449, pp. 1-9, 2019.

(Continued)

*Primary Examiner* — Anne M. Gussow
*Assistant Examiner* — Brianna K Swartwout
(74) *Attorney, Agent, or Firm* — ArentFox Schiff LLP; Daniel W. Clarke

(57) ABSTRACT

Provided is a T cell receptor (TCR) capable of specifically binding to KRAS G12V mutant antigens; the mutant antigen short peptide VVGAVGVGK is capable of forming a complex with HLA A1101, and the TCR specifically binds to said complex. Also provided in the present invention are a nucleic acid molecule encoding the TCR and a vector comprising the nucleic acid molecule. Also provided are TCR-transduced cells.

19 Claims, 10 Drawing Sheets

Specification includes a Sequence Listing.

(56) References Cited

OTHER PUBLICATIONS

Search Report and Written Opinion issued in SG Application No. 11202203614S on Jun. 25, 2024, 11 pages.

Chatani, P.D., et al., "Mutated RAS: Targeting the "Untargetable" with T-cells," Clin Cancer Res., vol. 26, No. 3, Sep. 2019, pp. 537-544.

Chen, F., et al., "Neoantigen identification strategies enable personalized immunotherapy in refractory solid tumors," The Journal of Clinical Investigation, vol. 129, No. 5, May 2019, pp. 2056-2070.

Wang, Q.J., et al., "Identification of T-cell Receptors Targeting KRAS-mutated Human Tumors," Cancer Immunol. Res., vol. 4, No. 3, Dec. 2015, pp. 204-214.

International Search Report of PCT Application No. PCT/CN2020/120191 mailed on Jan. 12, 2021, along with English language translation thereof.

* cited by examiner

QKEVEQNSGPLSVPEGAIASLNCTYSDRVSQSFFWYRQYSGKSPELIMSIYS
NGDKEDGRFTAQLNKASQYVSLLIRDSQPSDSATYLCASLKGNNDMRFGA
GTRLTVKP (SEQ ID NO: 1)

FIG. 1a

Cagaaggaggtggagcagaattctggacccctcagtgttccagagggagccattgcctctctcaactgcacttacagt
gaccgagtttcccagtccttcttctggtacagacaatattctgggaaaagccctgagttgataatgtccatatactccaatg
gtgacaaagaagatggaaggtttacagcacagctcaataaagccagccagtatgtttctctgctcatcagagactccca
gcccagtgattcagccacctacctctgtgcctccctcaagggtaacaatgacatgcgctttggagcagggaccagact
gacagtaaaacca (SEQ ID NO: 2)

FIG. 1b

QKEVEQNSGPLSVPEGAIASLNCTYSDRVSQSFFWYRQYSGKSPELIMSIYS
NGDKEDGRFTAQLNKASQYVSLLIRDSQPSDSATYLCASLKGNNDMRFGA
GTRLTVKPNIQNPDPAVYQLRDSKSSDKSVCLFTDFDSQTNVSQSKDSDVYI
TDKTVLDMRSMDFKSNSAVAWSNKSDFACANAFNNSIIPEDTFFPSPESSCD
VKLVEKSFETDTNLNFQNLSVIGFRILLLKVAGFNLLMTLRLWSS (SEQ ID
NO: 3)

FIG. 1c cagaaggaggtggagcagaattctggacccctcagtgttccagagggagccattgcctctctcaactgcacttacagt
gaccgagtttcccagtccttcttctggtacagacaatattctgggaaaagccctgagttgataatgtccatatactccaatg
gtgacaaagaagatggaaggtttacagcacagctcaataaagccagccagtatgtttctctgctcatcagagactccca
gcccagtgattcagccacctacctctgtgcctccctcaagggtaacaatgacatgcgctttggagcagggaccagact
gacagtaaaaccaaatAtccagaaccctgaccctgccgtgtaccagctgagagactctaaatccagtgacaagtctgt
ctgcctattcaccgattttgattctcaaacaaatgtgtcacaaagtaaggattctgatgtgtatatcacagacaaaactgtg
ctagacatgaggtctatggacttcaagagcaacagtgctgtggcctggagcaacaaatctgactttgcatgtgcaaacg
ccttcaacaacagcattattccagaagacaccttcttccccagcccagaaagttcctgtgatgtcaagctggtcgagaaa
agctttgaaacagatacgaacctaaactttcaaaacctgtcagtgattgggttccgaatcctcctcctgaaagtggccgg
gtttaatctgctcatgacgctgcggctgtggtccagc (SEQ ID NO: 4)

FIG. 1d

MKSLRVLLVILWLQLSWVWSQQKEVEQNSGPLSVPEGAIASLNCTYSDRVS
QSFFWYRQYSGKSPELIMSIYSNGDKEDGRFTAQLNKASQYVSLLIRDSQP
SDSATYLCASLKGNNDMRFGAGTRLTVKPNIQNPDPAVYQLRDSKSSDKSV
CLFTDFDSQTNVSQSKDSDVYITDKTVLDMRSMDFKSNSAVAWSNKSDFA
CANAFNNSIIPEDTFFPSPESSCDVKLVEKSFETDTNLNFQNLSVIGFRILLLK
VAGFNLLMTLRLWSS (SEQ ID NO: 22)

FIG. 1e atgaaatccttgagagttttactagtgatcctgtggcttcagttgagctgggtttggagccaacagaaggaggtggagca
gaattctggacccctcagtgttccagagggagccattgcctctctcaactgcacttacagtgaccgagtttcccagtcctt
cttctggtacagacaatattctgggaaaagccctgagttgataatgtccatatactccaatggtgacaaagaagatggaa
ggtttacagcacagctcaataaagccagccagtatgtttctctgctcatcagagactcccagcccagtgattcagccacc
tacctctgtgcctccctcaagggtaacaatgacatgcgctttggagcagggaccagactgacagtaaaaccaaatAtc
cagaaccctgaccctgccgtgtaccagctgagagactctaaatccagtgacaagtctgtctgcctattcaccgattttgat
tctcaaacaaatgtgtcacaaagtaaggattctgatgtgtatatcacagacaaaactgtgctagacatgaggtctatgga
cttcaagagcaacagtgctgtggcctggagcaacaaatctgactttgcatgtgcaaacgccttcaacaacagcattattc
cagaagacaccttcttccccagcccagaaagttcctgtgatgtcaagctggtcgagaaaagctttgaaacagatacgaa
cctaaactttcaaaacctgtcagtgattgggttccgaatcctcctcctgaaagtggccgggtttaatctgctcatgacgct
gcggctgtggtccagc (SEQ ID NO: 23)

FIG. 1f

GAGVSQSPRYKVAKRGQDVALRCDPISGHVSLFWYQQALGQGPEFLTYF
QNEAQLDKSGLPSDRFFAERPEGSVSTLKIQRTQQEDSAVYLCASSSSRW
EQQFFGPGTRLTVL (SEQ ID NO: 5)

FIG. 2a ggtgctggagtctcccagtcccctaggtacaaagtcgcaaagagaggacaggatgtagctctcaggtgtgatccaattt
cgggtcatgtatccctttttggtaccaacaggccctggggcaggggccagagtttctgacttatttccagaatgaagctc
aactagacaaatcgggggctgcccagtgatcgcttctttgcagaaaggcctgagggatccgtctccactctgaagatcca
gcgcacacagcaggaggactccgccgtgtatctctgtgccagcagctccagtaggtgggagcagcagttcttcgggc
cagggacacggctcaccgtgcta (SEQ ID NO: 6)

FIG. 2b

GAGVSQSPRYKVAKRGQDVALRCDPISGHVSLFWYQQALGQGPEFLTYFQ
NEAQLDKSGLPSDRFFAERPEGSVSTLKIQRTQQEDSAVYLCASSSSRWEQ
QFFGPGTRLTVLEDLKNVFPPEVAVFEPSEAEISHTQKATLVCLATGFYPDH
VELSWWVNGKEVHSGVSTDPQPLKEQPALNDSRYCLSSRLRVSATFWQNP
RNHFRCQVQFYGLSENDEWTQDRAKPVTQIVSAEAWGRADCGFTSESYQ
QGVLSATILYEILLGKATLYAVLVSALVLMAMVKRKDSRG (SEQ ID NO: 7)

FIG. 2c

Ggtgctggagtctcccagtcccctaggtacaaagtcgcaaagagaggacaggatgtagctctcaggtgtgatccaatt
tcgggtcatgtatccctttttttggtaccaacaggccctggggcaggggccagagtttctgacttatttccagaatgaagct
caactagacaaatcggggctgcccagtgatcgcttctttgcagaaaggcctgagggatccgtctccactctgaagatcc
agcgcacacagcaggaggactccgccgtgtatctctgtgccagcagctccagtaggtgggagcagcagttcttcggg
ccagggacacggctcaccgtgctaGaggacctgaaaaacgtgttcccacccgaggtcgctgtgtttgagccatcaga
agcagagatctcccacacccaaaaggccacactggtgtgcctggccacaggcttctaccccgaccacgtggagctg
agctggtgggtgaatgggaaggaggtgcacagtggggtcagcacagacccgcagcccctcaaggagcagcccgc
cctcaatgactccagatactgcctgagcagccgcctgagggtctcggccaccttctggcagaaccccgcaaccactt
ccgctgtcaagtccagttctacgggctctcggagaatgacgagtggacccaggatagggccaaacctgtcacccaga
tcgtcagcgccgaggcctggggtagagcagactgtggcttcacctccgagtcttaccagcaaggggtcctgtctgcca
ccatcctctatgagatcttgctagggaaggccaccttgtatgccgtgctggtcagtgccctcgtgctgatggccatggtc
aagagaaaggattccagaggc (SEQ ID NO: 8)

FIG. 2d

MGTRLLCWVVLGFLGTDHTGAGVSQSPRYKVAKRGQDVALRCDPISGHV
SLFWYQQALGQGPEFLTYFQNEAQLDKSGLPSDRFFAERPEGSVSTLKIQRT
QQEDSAVYLCASSSSRWEQQFFGPGTRLTVLEDLKNVFPPEVAVFEPSEAEI
SHTQKATLVCLATGFYPDHVELSWWVNGKEVHSGVSTDPQPLKEQPALND
SRYCLSSRLRVSATFWQNPRNHFRCQVQFYGLSENDEWTQDRAKPVTQIV
SAEAWGRADCGFTSESYQQGVLSATILYEILLGKATLYAVLVSALVLMAMV
KRKDSRG (SEQ ID NO: 24)

FIG. 2e atgggcaccaggctcctctgctgggtggtcctgggtttcctagggacagatcacacaggtgctggagtctcccagtcc
cctaggtacaaagtcgcaaagagaggacaggatgtagctctcaggtgtgatccaatttcgggtcatgtatccctttttttgg
taccaacaggccctggggcaggggccagagtttctgacttatttccagaatgaagctcaactagacaaatcggggctg
cccagtgatcgcttctttgcagaaaggcctgagggatccgtctccactctgaagatccagcgcacacagcaggagga
ctccgccgtgtatctctgtgccagcagctccagtaggtgggagcagcagttcttcgggccagggacacggctcaccgt
gctaGaggacctgaaaaacgtgttcccacccgaggtcgctgtgtttgagccatcagaagcagagatctcccacaccc
aaaaggccacactggtgtgcctggccacaggcttctaccccgaccacgtggagctgagctggtgggtgaatgggaa
ggaggtgcacagtggggtcagcacagacccgcagcccctcaaggagcagcccgccctcaatgactccagatactg
cctgagcagccgcctgagggtctcggccaccttctggcagaacccccgcaaccacttccgctgtcaagtccagttcta
cgggctctcggagaatgacgagtggacccaggatagggccaaacctgtcacccagatcgtcagcgccgaggcctg
gggtagagcagactgtggcttcacctccgagtcttaccagcaaggggtcctgtctgccaccatcctctatgagatcttgc
tagggaaggccaccttgtatgccgtgctggtcagtgccctcgtgctgatggccatggtcaagagaaaggattccagag
gc (SEQ ID NO: 25)

FIG. 2f

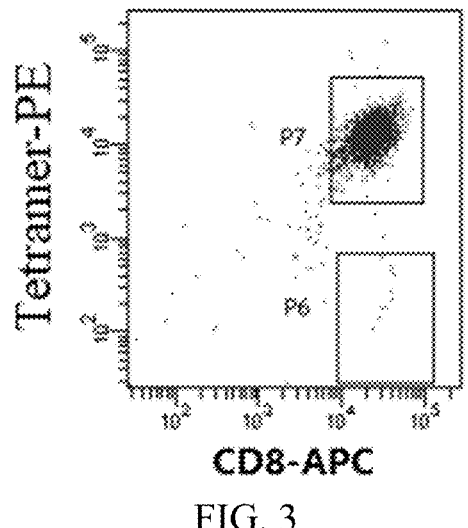

FIG. 3

MQKEVEQNSGPLSVPEGAIASLNCTYSDRVSQSFFWYRQYSGKSPELIMS
IYSNGDKEDGRFTAQLNKASQYVSLLIRDSQPSDSATYLCASLKGNNDM
RFGAGTRLTVKPNIQNPDPAVYQLRDSKSSDKSVCLFTDFDSQTNVSQSK
DSDVYITDKCVLDMRSMDFKSNSAVAWSNKSDFACANAFNNSIIPEDTFF
PSPESS (SEQ ID NO: 26)

FIG. 4a

ATGCAGAAAGAAGTGGAACAGAATTCTGGACCCCTCAGTGTTCCAGAG
GGAGCCATTGCCTCTCTCAACTGCACTTACAGTGACCGAGTTTCCCAGT
CCTTCTTCTGGTACAGACAATATTCTGGGAAAAGCCCTGAGTTGATAATG
TCCATATACTCCAATGGTGACAAAGAAGATGGAAGGTTTACAGCACAGC
TCAATAAAGCCAGCCAGTATGTTTCTCTGCTCATCAGAGACTCCCAGCCC
AGTGATTCAGCCACCTACCTCTGTGCCTCCCTCAAGGGTAACAATGACAT
GCGCTTTGGAGCAGGGACCAGACTGACAGTAAAACCAAATATCCAGAA
CCCTGACCCTGCCGTGTACCAGCTGAGAGACTCTAAGTCGAGTGACAAG
TCTGTCTGCCTATTCACCGATTTTGATTCTCAAACAAATGTGTCACAAAG
TAAGGATTCTGATGTGTATATCACAGACAAATGTGTGCTAGACATGAGGT
CTATGGACTTCAAGAGCAACAGTGCTGTGGCCTGGAGCAACAAATCTGA
CTTTGCATGTGCAAACGCCTTCAACAACAGCATTATTCCAGAAGACACC
TTCTTCCCCAGCCCAGAAAGTTCCTAA (SEQ ID NO: 27)

FIG. 4b

MGAGVSQSPRYKVAKRGQDVALRCDPISGHVSLFWYQQALGQGPEFLTYF
QNEAQLDKSGLPSDRFFAERPEGSVSTLKIQRTQQEDSAVYLCASSSSRWE
QQFFGPGTRLTVLEDLKNVFPPEVAVFEPSEAEISHTQKATLVCLATGFYPD
HVELSWWVNGKEVHSGVCTDPQPLKEQPALNDSRYALSSRLRVSATFWQD
PRNHFRCQVQFYGLSENDEWTQDRAKPVTQIVSAEAWGRAD (SEQ ID NO:
28)

FIG. 5a

ATGGGTGCAGGTGTTAGCCAGTCCCCTAGGTACAAAGTCGCAAAGAGA
GGACAGGATGTAGCTCTCAGGTGTGATCCAATTTCGGGTCATGTATCCCT
TTTTTGGTACCAACAGGCCCTGGGGCAGGGGCCAGAGTTTCTGACTTAT
TTCCAGAATGAAGCTCAACTAGACAAATCGGGGCTGCCCAGTGATCGCT
TCTTTGCAGAAAGGCCTGAGGGATCCGTCTCCACTCTGAAGATCCAGCG
CACACAGCAGGAGGACTCCGCCGTGTATCTCTGTGCCAGCAGCTCCAGT
AGGTGGGAGCAGCAGTTCTTCGGGCCAGGGACACGGCTCACCGTGCTA
GAGGACCTGAAAAACGTGTTCCCACCCGAGGTCGCTGTGTTTGAGCCAT
CAGAAGCAGAGATCTCCCACACCCAAAAGGCCACACTGGTGTGCCTGG
CCACCGGTTTCTACCCCGACCACGTGGAGCTGAGCTGGTGGGTGAATGG
GAAGGAGGTGCACAGTGGGGTCTGCACAGACCCGCAGCCCCTCAAGGA
GCAGCCCGCCCTCAATGACTCCAGATACGCTCTGAGCAGCCGCCTGAGG
GTCTCGGCCACCTTCTGGCAGGACCCCCGCAACCACTTCCGCTGTCAAG
TCCAGTTCTACGGGCTCTCGGAGAATGACGAGTGGACCCAGGATAGGGC
CAAACCCGTCACCCAGATCGTCAGCGCCGAGGCCTGGGGTAGAGCAGA
CTAA (SEQ ID NO: 29)

FIG. 5b

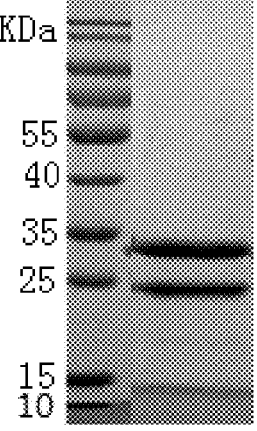

FIG. 6a

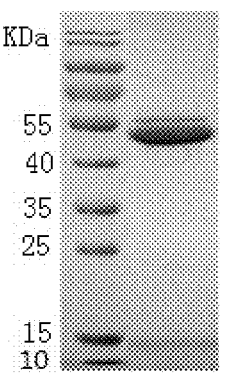

FIG. 6b

QKEVEQNSGPLSVPEGENVSINCTYSDRVSQSFFWYRQYSGKSPELIMSIYS
NGDKEDGRFTAQLNKASQYVSLEIRDVQPSDSATYLCASLKGNNDMRFGA
GTRLTVKPGGGSEGGGSEGGGSEGGGSEGGTGGAGVSQSPRYLSVKRGQD
VTLRCDPISGHVSLFWYQQAPGQGPEFLTYFQNEAQLDKSGLPSDRFNAER
PEGSVSTLKIQRVQPEDSAVYLCASSSSRWEQQFFGPGTRLTVD (SEQ ID
NO: 30)

FIG. 7a

CAGAAAGAGGTGGAACAAAACAGCGGTCCGCTGAGCGTGCCGGAGGG
TGAAAACGTTAGCATCAACTGCACCTACAGCGACCGTGTTAGCCAGAGC
TTCTTTTGGTACCGTCAATATAGCGGTAAAAGCCCGGAGCTGATCATGAG
CATTTATAGCAACGGTGACAAGGAAGATGGCCGTTTCACCGCGCAGCTG
AACAAAGCGAGCCAATACGTGAGCCTGGAGATTCGTGACGTTCAGCCG
AGCGATAGCGCGACCTATCTGTGCGCGAGCCTGAAGGGTAACAACGATA
TGCGTTTTGGTGCGGGCACCCGTCTGACCGTGAAACCGGGTGGCGGTA
GCGAGGGCGGTGGCAGCGAAGGTGGCGGTAGCGAGGGCGGTGGCAGC
GAAGGTGGCACCGGTGGCGCGGGTGTGAGCCAGAGCCCGCGTTACCTG
AGCGTGAAGCGTGGTCAAGACGTTACCCTGCGTTGCGATCCGATCAGCG
GCCACGTTAGCCTGTTCTGGTATCAGCAAGCGCCGGGTCAGGGTCCGGA
GTTCCTGACCTATTTTCAGAACGAAGCGCAACTGGACAAGAGCGGTCTG
CCGAGCGATCGTTTTAACGCGGAGCGTCCGGAAGGCAGCGTGAGCACC
CTGAAAATTCAGCGTGTGCAACCGGAGGACAGCGCGGTTTATCTGTGCG
CGAGCAGCAGCAGCCGTTGGGAACAGCAATTCTTTGGTCCGGGTACCC
GCCTGACCGTTGAT (SEQ ID NO: 31)

FIG. 7b

QKEVEQNSGPLSVPEGENVSINCTYSDRVSQSFFWYRQYSGKSPELIMSIYS
NGDKEDGRFTAQLNKASQYVSLEIRDVQPSDSATYLCASLKGNNDMRFGA
GTRLTVKP (SEQ ID NO: 32)

FIG. 8a

CAGAAAGAGGTGGAACAAAACAGCGGTCCGCTGAGCGTGCCGGAGGG
TGAAAACGTTAGCATCAACTGCACCTACAGCGACCGTGTTAGCCAGAGC
TTCTTTTGGTACCGTCAATATAGCGGTAAAAGCCCGGAGCTGATCATGAG
CATTTATAGCAACGGTGACAAGGAAGATGGCCGTTTCACCGCGCAGCTG
AACAAAGCGAGCCAATACGTGAGCCTGGAGATTCGTGACGTTCAGCCG
AGCGATAGCGCGACCTATCTGTGCGCGAGCCTGAAGGGTAACAACGATA
TGCGTTTTGGTGCGGGCACCCGTCTGACCGTGAAACCG (SEQ ID NO: 33)

FIG. 8b

GAGVSQSPRYLSVKRGQDVTLRCDPISGHVSLFWYQQAPGQGPEFLTYFQ
NEAQLDKSGLPSDRFNAERPEGSVSTLKIQRVQPEDSAVYLCASSSSRWEQ
QFFGPGTRLTVD (SEQ ID NO: 34)

FIG. 9a

GGCGCGGGTGTGAGCCAGAGCCCGCGTTACCTGAGCGTGAAGCGTGGT
CAAGACGTTACCCTGCGTTGCGATCCGATCAGCGGCCACGTTAGCCTGT
TCTGGTATCAGCAAGCGCCGGGTCAGGGTCCGGAGTTCCTGACCTATTT
TCAGAACGAAGCGCAACTGGACAAGAGCGGTCTGCCGAGCGATCGTTT
TAACGCGGAGCGTCCGGAAGGCAGCGTGAGCACCCTGAAAATTCAGCG
TGTGCAACCGGAGGACAGCGCGGTTTATCTGTGCGCGAGCAGCAGCAG
CCGTTGGGAACAGCAATTCTTTGGTCCGGGTACCCGCCTGACCGTTGAT
(SEQ ID NO: 35)

FIG. 9b

GGGSEGGGSEGGGSEGGGSEGGTG (SEQ ID NO: 36)

FIG. 10a

GGTGGCGGTAGCGAGGGCGGTGGCAGCGAAGGTGGCGGTAGCGAGGG
CGGTGGCAGCGAAGGTGGCACCGGT (SEQ ID NO: 37)

FIG. 10b

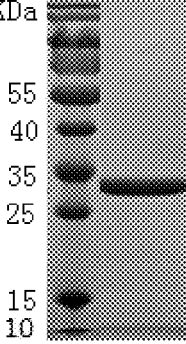

FIG. 11

Time (second)

T CELL RECEPTOR RECOGNISING KRAS MUTATION AND ENCODING SEQUENCE THEREOF

CROSS-REFERENCE TO RELATED APPLICATIONS

This application is a National Stage Application, filed under 35 U.S.C. § 371, of International Application No. PCT/CN2020/120191, filed Oct. 10, 2020, which claims the benefit of priority under 35 U.S.C. § 119 to CN application No. 201910960523.3, filed Oct. 10, 2019, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 6, 2022 is named 51766-505N01US_ST25_Sequence.txt and is 34 KB in size.

TECHNICAL FIELD

The present disclosure relates to a T-cell receptor (TCR) capable of recognising a short peptide derived from a KRAS G12V antigen and an encoding sequence thereof. The present disclosure also relates to KRAS G12V-specific T cells obtained by transducing the TCR and use thereof in the prevention and treatment of diseases related to KRAS G12V.

BACKGROUND

KRAS gene (p21 gene) is a rat sarcoma virus oncogene, which is about 35 kb long and located on chromosome 12. It is a member of ras gene family and encodes the KRAS protein. The KRAS gene can be divided into the wild-type KRAS gene or the mutant-type KRAS gene. Under normal conditions, the wild-type KRAS can control the pathway of regulating the cell growth. Once the wild-type KRAS mutates, it will continuously stimulate the cell growth and cause tumor. The common mutation sites of the KRAS gene are located at codons 12 and 13 of exon 2 of the KRAS gene, among which G12V is one of the seven common mutation sites (Chin J Lab Med. November 2012, Vol. 35, No. 11). The KRAS protein encoded by the KRAS mutant (mKRAS) will be continuously activated, and then the cell proliferation will be out of control, resulting in the formation of tumors. Studies have shown that KRAS-G12V is related to a variety of human malignant tumors, comprising but not limited to lung cancer and colorectal cancer (Tumour Biol. 2016 May; 37 (5): 6823-30), pancreatic cancer, gastric cancer (J Cancer 2019; 10 (4): 821-828), etc., and tumor patients with KRAS-G12V mutation have the shortest survival time (Br J Cancer. 2015 Oct. 20; 113(8): 1206-1215). VVGAVGVGK (SEQ ID NO: 9) or VVVGAVGVGK (SEQ ID NO: 38) is a short peptide derived from the KRAS G12V antigen and is a target for the treatment of KRAS G12V-related diseases.

T cell adoptive immunotherapy is to transfer reactive T cells with specificity for target cell antigen into patients to make theses reactive T cells act on target cells. T-cell receptor (TCR) is a membrane protein on the surface of T cells, which can recognise the corresponding antigenic peptides on the surface of target cells. In the immune system, once antigen-specific TCRs bind to peptide-Major Histocompatibility Complexes (pMHC complexes), it causes direct physical contact of a T cell and an antigen-presenting cell (APC). Then, the interaction of other membrane molecules in both of the T cell and APC occurs and the subsequent cell signaling and other physiological responses are initiated so that a range of different antigen-specific T cells exert immune effects on their target cells. Therefore, those skilled in the art are committed to isolating TCRs that are specific for KRAS G12V antigen mutation short peptides and transducing T cells with such TCRs to obtain T cells having specificity for KRAS G12V antigen short peptides, so that they function in cellular immunotherapy.

SUMMARY

The object of the present disclosure is to provide a T-cell receptor capable of recognising a KRAS G12V antigen short peptide.

In a first aspect of the present disclosure, a T-cell receptor (TCR) is provided, which is capable of specifically binding to a VVGAVGVGK-HLA A1101 complex.

In another preferred embodiment, the TCR comprises a TCRα chain variable domain and a TCRβ chain variable domain, an amino acid sequence of CDR3 of the TCRα chain variable domain is ASLKGNNDMR (SEQ ID NO: 12); and/or an amino acid sequence of CDR3 of the TCRβ chain variable domain is ASSSSRWEQQF (SEQ ID NO: 15).

In another preferred embodiment, three complementarity determining regions (CDRs) of the TCRα chain variable domain are:

```
                                    (SEQ ID NO: 10)
       α CDR1-DRVSQS;

(SEQ ID NO: 11)
       α CDR2-IYSNGD;
       and (SEQ ID NO: 12)
       α CDR3- ASLKGNNDMR;
``` and/or
three CDRs of the TCRβ chain variable domain are:

```
                                    (SEQ ID NO: 13)
       β CDR1- SGHVS;

(SEQ ID NO: 14)
       β CDR2- FQNEAQ;
       and (SEQ ID NO: 15)
       β CDR3- ASSSSRWEQQF.
```

In another preferred embodiment, the TCR is also capable of specifically binding to a VVVGAVGVGK-HLA A1101 complex.

In another preferred embodiment, the TCR comprises a TCRα chain variable domain and a TCRβ chain variable domain, where the TCRα chain variable domain is an amino acid sequence having at least 90% of sequence identity with SEQ ID NO: 1; and/or the TCRβ chain variable domain is an amino acid sequence having at least 90% of sequence identity with SEQ ID NO: 5.

In another preferred embodiment, the TCR comprises an α chain variable domain amino acid sequence SEQ ID NO: 1.

In another preferred embodiment, the TCR comprises a β chain variable domain amino acid sequence SEQ ID NO: 5.

In another preferred embodiment, the TCR is an αβ heterodimer and comprises a TCRα chain constant region TRAC*01 and a TCRβ chain constant region TRBC1*01 or TRBC2*01.

In another preferred embodiment, the α chain amino acid sequence of the TCR is SEQ ID NO: 3 and/or the β chain amino acid sequence of the TCR is SEQ ID NO: 7.

In another preferred embodiment, the TCR is soluble.

In another preferred embodiment, the TCR is a single chain.

In another preferred embodiment, the TCR is formed by linking the α chain variable domain and the β chain variable domain by a peptide linker sequence.

In another preferred embodiment, the TCR has one or more mutations in an α chain variable region amino acid at position 11, 13, 19, 21, 53, 76, 89, 91 or 94, and/or an α chain J gene short peptide amino acid at reciprocal position 3, 5 or 7; and/or the TCR has one or more mutations in a β chain variable region amino acid at position 11, 13, 19, 21, 53, 76, 89, 91 or 94, and/or a β chain J gene short peptide amino acid at reciprocal position 2, 4 or 6, wherein the positions in an amino acid sequence are numbered according to the position numbers listed in the International Immunogenetics Information System (IMGT).

In another preferred embodiment, the α chain variable domain amino acid sequence of the TCR comprises SEQ ID NO: 32 and/or the β chain variable domain amino acid sequence of the TCR comprises SEQ ID NO: 34.

In another preferred embodiment, the amino acid sequence of the TCR is SEQ ID NO: 30.

In another preferred embodiment, the TCR comprises (a) all or part of the TCR α chain other than its transmembrane domain; and (b) all or part of the TCR β chain other than its transmembrane domain; and (a) and (b) each comprise a functional variable domain, or comprise at least part of a functional variable domain and the TCR chain constant domain.

In another preferred embodiment, cysteine residues form an artificial disulfide bond between the α and β chain constant domains of the TCR.

In another preferred embodiment, the cysteine residues forming the artificial disulfide bond in the TCR are substituted for one or more groups of amino acids selected from the following:

Thr48 of TRAC*01 exon 1 and Ser57 of TRBC1*01 or TRBC2*01 exon 1;

Thr45 of TRAC*01 exon 1 and Ser77 of TRBC1*01 or TRBC2*01 exon 1;

Tyr10 of TRAC*01 exon 1 and Ser17 of TRBC1*01 or TRBC2*01 exon 1;

Thr45 of TRAC*01 exon 1 and Asp59 of TRBC1*01 or TRBC2*01 exon 1;

Ser15 of TRAC*01 exon 1 and Glu15 of TRBC1*01 or TRBC2*01 exon 1;

Arg53 of TRAC*01 exon 1 and Ser54 of TRBC1*01 or TRBC2*01 exon 1;

Pro89 of TRAC*01 exon 1 and Ala19 of TRBC1*01 or TRBC2*01 exon 1; and

Tyr10 of TRAC*01 exon 1 and Glu20 of TRBC1*01 or TRBC2*01 exon 1.

In another preferred embodiment, the α chain amino acid sequence of the TCR is SEQ ID NO: 26 and/or the β chain amino acid sequence of the TCR is SEQ ID NO: 28.

In another preferred embodiment, an artificial interchain disulfide bond is contained between an α chain constant region and a β chain constant region of the TCR.

In another preferred embodiment, cysteine residues forming the artificial interchain disulfide bond in the TCR are substituted for one or more groups of amino acids selected from the following:

an amino acid at position 46 of TRAV and an amino acid at position 60 of TRBC1*01 or TRBC2*01 exon 1;

an amino acid at position 47 of TRAV and an amino acid at position 61 of TRBC1*01 or TRBC2*01 exon 1;

an amino acid at position 46 of TRAV and an amino acid at position 61 of TRBC1*01 or TRBC2*01 exon 1; or an amino acid at position 47 of TRAV and an amino acid at position 60 of TRBC1*01 or TRBC2*01 exon 1.

In another preferred embodiment, the TCR comprises an α chain variable domain, a β chain variable domain and all or part of a β chain constant domain other than its transmembrane domain, which, however, does not comprise an α chain constant domain, and the α chain variable domain of the TCR and the β chain form a heterodimer.

In another preferred embodiment, a conjugate binds to the α chain and/or β chain of the TCR at C- or N-terminal.

In another preferred embodiment, the conjugate that binds to the TCR is a detectable label, a therapeutic agent, a PK modified moiety or a combination of any of these substances. Preferably, the therapeutic agent is an anti-CD3 antibody.

In a second aspect of the present disclosure, a multivalent TCR complex comprising at least two TCR molecules is provided, and wherein at least one TCR molecule is the TCR of the first aspect of the present disclosure.

In a third aspect of the present disclosure, a nucleic acid molecule is provided, which comprises a nucleic acid sequence encoding the TCR molecule of the first aspect of the present disclosure or a complement sequence thereof.

In another preferred embodiment, the nucleic acid molecule comprises a nucleotide sequence SEQ ID NO: 2 or SEQ ID NO: 33 encoding the TCRα chain variable domain.

In another preferred embodiment, the nucleic acid molecule comprises a nucleotide sequence SEQ ID NO: 6 or SEQ ID NO: 35 encoding the TCRβ chain variable domain.

In another preferred embodiment, the nucleic acid molecule comprises a nucleotide sequence SEQ ID NO: 4 encoding the TCRα chain and/or comprises a nucleotide sequence SEQ ID NO: 8 encoding the TCRβ chain.

In a fourth aspect of the present disclosure, a vector is provided, which comprises the nucleic acid molecule of the third aspect of the present disclosure; preferably, the vector is a virus vector; and more preferably, the vector is a lentiviral vector.

In a fifth aspect of the present disclosure, an isolated host cell is provided, which comprises the vector of the fourth aspect of the present disclosure or having the exogenous nucleic acid molecule of the third aspect of the present disclosure integrated into its genome.

In a sixth aspect of the present disclosure, a cell is provided, which is transduced with the nucleic acid molecule of the third aspect of the present disclosure or the vector of the fourth aspect of the present disclosure; and preferably, the cell is a T cell or a stem cell.

In a seventh aspect of the present disclosure, a pharmaceutical composition is provided, which comprises a pharmaceutically acceptable carrier, and the TCR of the first aspect of the present disclosure, or the TCR complex of the second aspect of the present disclosure, or the nucleic acid molecule of the third aspect of the present disclosure, or the vector of the fourth aspect of the present disclosure, or the cell of the sixth aspect of the present disclosure.

In an eighth aspect of the present disclosure, use of the T-cell receptor (TCR) of the first aspect of the present disclosure, or the TCR complex of the second aspect of the present disclosure, the nucleic acid molecule of the third aspect of the present disclosure, or the vector of the fourth aspect of the present disclosure, or the cell of the sixth aspect of the present disclosure for preparing a medicament for treating tumor or autoimmune diseases is provided. Preferably, the tumor is pancreatic cancer, colon cancer, rectal cancer or lung cancer.

In a ninth aspect of the present disclosure, a medicament for treating tumor or autoimmune diseases using the T-cell receptor (TCR) of the first aspect of the present disclosure, or the TCR complex of the second aspect of the present disclosure, the nucleic acid molecule of the third aspect of the present disclosure, or the vector of the fourth aspect of the present disclosure, or the cell of the sixth aspect of the present disclosure is provided. Preferably, the tumor is pancreatic cancer, colon cancer, rectal cancer or lung cancer.

In a tenth aspect of the present disclosure, a method for treating a disease is provided, which comprises administering an appropriate amount of the T-cell receptor (TCR) of the first aspect of the present disclosure, or the TCR complex of the second aspect of the present disclosure, the nucleic acid molecule of the third aspect of the present disclosure, or the vector of the fourth aspect of the present disclosure, or the cell of the sixth aspect of the present disclosure, or the pharmaceutical composition of the seventh aspect of the present disclosure to a subject in need thereof;

preferably, the disease is tumor; and more preferably, the tumor is pancreatic cancer, colon cancer, rectal cancer or lung cancer.

It is to be understood that within the scope of the present disclosure, the various technical features of the present disclosure and the technical features specifically described hereinafter (as in the embodiments) may be combined with each other to constitute a new or preferred technical solution, which will not be repeated herein one by one.

BRIEF DESCRIPTION OF DRAWINGS

FIGS. 1a, 1b, 1c, 1d, 1e, and 1f show a TCRα chain variable domain amino acid sequence, a TCRα chain variable domain nucleotide sequence, a TCRα chain amino acid sequence, a TCRα chain nucleotide sequence, a TCRα chain amino acid sequence having a leader sequence, and a TCRα chain nucleotide sequence having a leader sequence, respectively.

FIGS. 2a, 2b, 2c, 2d, 2e, and 2f show a TCRβ chain variable domain amino acid sequence, a TCRβ chain variable domain nucleotide sequence, a TCRβ chain amino acid sequence, a TCRβ chain nucleotide sequence, a TCRβ chain amino acid sequence having a leader sequence, and a TCRβ chain nucleotide sequence having a leader sequence, respectively.

FIG. 3 shows results of CD8$^+$ and tetramer-PE double positive staining of monoclonal cells.

FIGS. 4a and 4b are an amino acid sequence and a nucleotide sequence of a soluble TCRα chain, respectively.

FIGS. 5a and 5b are an amino acid sequence and a nucleotide sequence of a soluble TCRβ chain, respectively.

FIGS. 6a and 6b are gel diagrams of a soluble TCR obtained after purification, wherein the right lanes in FIGS. 6a and 6b are a reduced gel and a non-reduced gel, respectively, and the left lanes are molecular weight markers.

FIGS. 7a and 7b are an amino acid sequence and a nucleotide sequence of a single chain TCR, respectively.

FIGS. 8a and 8b are an amino acid sequence and a nucleotide sequence of a single chain TCRα chain variable domain, respectively.

FIGS. 9a and 9b are an amino acid sequence and a nucleotide sequence of a single chain TCRβ chain variable domain, respectively.

FIGS. 10a and 10b are an amino acid sequence and a nucleotide sequence of a single chain TCR linker, respectively.

FIG. 11 is a gel diagram of a soluble single chain TCR obtained after purification, wherein the left lane is a molecular weight marker, and the right lane is a non-reducing gel.

DETAILED DESCRIPTION

Figure 12:
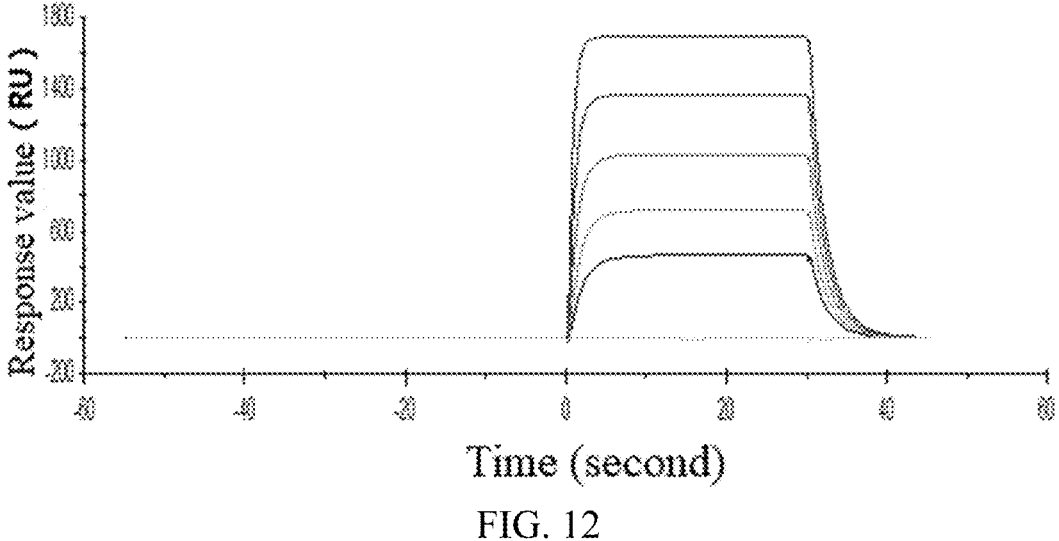
FIG. 12 is a BIAcore kinetic map of the binding of a soluble TCR to a VVGAVGVGK-HLA A1101 complex in the present disclosure.

Through extensive and intensive researches, the present disclosure obtains a T-cell receptor (TCR) capable of specifically binding to a KRAS G12V antigen short peptide VVGAVGVGK (SEQ ID NO: 9) or VVVGAVGVGK (SEQ ID NO: 38), and the antigen short peptide VVGAVGVGK or VVVGAVGVGK can respectively form a complex with HLA A1101 and be presented to the surface of cells. The present disclosure also provides a nucleic acid molecule encoding the TCR and a vector containing the nucleic acid molecule. In addition, the present disclosure also provides a cell transduced with the TCR of the present disclosure.

Term

Major histocompatibility complex (MHC) molecule is a protein of the immunoglobulin superfamily, which can be MHC molecule class I or MHC molecule class II. Therefore, the MHC molecule is specific for the antigen presentation. Different individuals have different MHCs, thereby presenting different short peptides in one protein antigen to the surface of respective APC cells. Human MHC is commonly referred to as HLA gene or HLA complex.

T-cell receptor (TCR) is the only receptor for presenting specific peptide antigens in Major histocompatibility complex (MHC). In the immune system, once antigen-specific TCRs bind to pMHC complexes, it causes direct physical contact of a T-cell and an antigen-presenting cell (APC). Then, the interaction of other membrane molecules in the T cell and APC occurs and the subsequent cell signaling and other physiological responses are initiated so that a range of different antigen-specific T cells exert immune effects on their target cells.

The TCR is a glycoprotein on the surface of cell membrane that exists in the form of α chain/β chain or γ chain/δ chain heterodimeric. The TCR heterodimer in 95% T cells consists of an α chain and a β chain, while 5% T cells has the TCR consisting of a γ chain and a δ chain. A native αβ heterodimeric TCR has an α chain and a β chain, and the α chain and the β chain form the subunit of the αβ heterodimeric TCR. Generally speaking, the α chain and the β chain each comprises a variable region, a linker region and a constant region, and the β chain typically also contains a short diversity region between the variable region and linker region, which however is often considered as a part of the linker region. Each variable region comprises three complementarity determining regions (CDRs), CDR1, CDR2 and CDR3, which are chimeric in the framework regions. The CDR regions determine the binding of the TCR to a pMHC complex, in which CDR3 is reconstructed by a variable region and a linker region, which is called hypervariable region. The α and β chains of the TCR are generally considered as having two "domains" respectively, that is, a variable domain and a constant domain. The variable domain consists of a variable region and a linker region linked to each other. The sequence of the constant region of the TCR may be found in the disclosed International ImMunoGeneTics Information System (IMGT) database, for example, the sequence of the constant domain of the α chain of the TCR molecule is "TRAC*01", and the sequence of the constant domain of the β chain of the TCR molecule is "TRBC1*01" or "TRBC2*01". In addition, the α and β chains of the TCR also contain a transmembrane domain and a cytoplasm domain, and the cytoplasm domain is very short.

In the present disclosure, the terms "polypeptide of the present disclosure", "TCR of the present disclosure" and "T-cell receptor of the present disclosure" are used interchangeably.

Natural Interchain Disulfide Bond and Artificial Interchain Disulfide Bond

A group of disulfide bonds is present between the Ca and CP chains in the membrane proximal region of a native TCR, which is named herein as "natural interchain disulfide bond". In the present disclosure, an interchain covalent disulfide bond which is artificially introduced and the position of which is different from the position of a natural interchain disulfide bond is named as "artificial interchain disulfide bond".

In order to describe the position of the disulfide bond conveniently, in the present disclosure, the positions of the amino acid sequences of TRAC*01 and TRBC1*01 or TRBC2*01 are sequentially numbered in order from N-terminal to C-terminal. For example, the 60th amino acid in the order from N-terminal to C-terminal in TRBC1*01 or TRBC2*01 is P (valine), which can be described as Pro60 of TRBC1*01 or TRBC2*01 exon 1 in the present disclosure, and can also be expressed as the amino acid at position 60 of TRBC1*01 or TRBC2*01 exon 1.

For another example, the 61st amino acid in the order from N-terminal to C-terminal in TRBC1*01 or TRBC2*01 is Q (glutamine), which can be described as Gln61 of TRBC1*01 or TRBC2*01 exon 1 in the present disclosure, and can also be expressed as the amino acid at position 61 of TRBC1*01 or TRBC2*01 exon 1, and so on. In the present disclosure, the positions of the amino acid sequences of variable regions TRAV and TRBV are numbered according to the positions listed in IMGT. As for an amino acid in TRAV, the position is numbered as 46 in IMGT, which is described in the present disclosure as the amino acid at position 46 of TRAV, and so on. In the present disclosure, if the sequence positions of other amino acids are specifically described, the special description shall prevail.

8

Detailed Description of the Present Disclosure

TCR Molecule

In the process of antigen processing, antigens are degraded in cells and then carried to the cell surface through MHC molecules. The T-cell receptors can recognise peptide-MHC complexes on the surface of antigen-presenting cells. Accordingly, a first aspect of the present disclosure provides a TCR molecule capable of binding to a VVGAVGVGK-HLA A1101 or VVVGAVGVGK-HLA A1101 complex. Preferably, the TCR molecule is isolated or purified. The α and β chains of the TCR each have three complementary determining regions (CDRs).

In a preferred embodiment of the present disclosure, the α chain of the TCR comprises CDRs having the following amino acid sequences:

```
                                    (SEQ ID NO: 10)
        α CDR1-DRVSQS;

(SEQ ID NO: 11)
        α CDR2-IYSNGD;
        and (SEQ ID NO: 12)
        α CDR3- ASLKGNNDMR;
``` and/or
three CDRs of the TCRβ chain variable domain are:

```
                                    (SEQ ID NO: 13)
        β CDR1- SGHVS;

(SEQ ID NO: 14)
        β CDR2- FQNEAQ;
        and (SEQ ID NO: 15)
        β CDR3- ASSSSRWEQQF.
```

The amino acid sequences of the above CDR regions of the present disclosure are chimeric in any suitable framework structure to prepare a chimeric TCR. As long as the framework structure is compatible with the CDR regions of the TCR of the present disclosure, those skilled in the art can design or synthesize TCR molecules having corresponding functions according to the CDR regions disclosed by the present disclosure. Therefore, the TCR molecule of the present disclosure refers to a TCR molecule comprising the CDR region sequences of the above α and/or β chains and any suitable framework structure. The TCRα chain variable domain of the present disclosure is an amino acid sequence having at least 90%, preferably 95%, more preferably 98%, of sequence identity with SEQ ID NO: 1; and/or the TCRβ chain variable domain of the present disclosure is an amino acid sequence having at least 90%, preferably 95%, more preferably 98%, of sequence identity with SEQ ID NO: 5.

In a preferred embodiment of the present disclosure, the TCR molecule of the present disclosure is a heterodimer consisting of an α chain and a β chain. Specifically, in one aspect, the α chain of the heterodimeric TCR molecule comprises a variable region and a constant region, and the amino acid sequence of the α chain variable domain comprises CDR1 (SEQ ID NO: 10), CDR2 (SEQ ID NO: 11) and CDR3 (SEQ ID NO: 12) of the above α chain. Preferably, the TCR molecule comprises an α chain variable domain amino acid sequence SEQ ID NO: 1. More preferably, the α chain variable domain amino acid sequence of the TCR molecule is SEQ ID NO: 1. In another aspect, the β chain of the heterodimeric TCR molecule comprises a variable region and a constant region, and the amino acid sequence of the β chain variable domain comprises CDR1 (SEQ ID NO: 13), CDR2 (SEQ ID NO: 14) and CDR3 (SEQ ID NO: 15) of the above β chain. Preferably, the TCR molecule comprises a β chain variable domain amino acid sequence SEQ ID NO: 15. More preferably, the β chain variable domain amino acid sequence of the TCR molecule is SEQ ID NO: 5.

In a preferred embodiment of the present disclosure, the TCR molecule of the present disclosure is a single chain TCR molecule consisting of all or part of an α chain and/or all or part of a β chain. For the description of the single chain TCR molecule, reference may be made to Chung et al (1994) Proc. Natl. Acad. Sci. USA 91, 12654-12658. As described in the literature, those skilled in the art can easily construct a single chain TCR molecule comprising the CDR regions of the present disclosure. Specifically, the single chain TCR molecule comprises Vα, Vβ, and Cβ which are, preferably, linked to each other in the order from N-terminal to C-terminal.

The amino acid sequence of the α chain variable domain of the single chain TCR molecule comprises CDR1 (SEQ ID NO: 10), CDR2 (SEQ ID NO: 11) and CDR3 (SEQ ID NO: 12) of the above α chain. Preferably, the single chain TCR molecule comprises an α chain variable domain amino acid sequence SEQ ID NO: 1. More preferably, the α chain variable domain amino acid sequence of the single chain TCR molecule is SEQ ID NO: 1. The β chain variable domain amino acid sequence of the single chain TCR molecule comprises CDR1 (SEQ ID NO: 13), CDR2 (SEQ ID NO: 14) and CDR3 (SEQ ID NO: 15) of the above α chain. Preferably, the single chain TCR molecule comprises a β chain variable domain amino acid sequence SEQ ID NO: 5. More preferably, the β chain variable domain amino acid sequence of the single chain TCR molecule is SEQ ID NO: 5.

In a preferred embodiment of the present disclosure, the constant domain of the TCR molecule of the present disclosure is a human constant domain. Those skilled in the art are aware of or may obtain a human constant domain amino acid sequence by consulting a related book or a disclosed IMGT (International Immunogenetics Information System) database. For example, the constant domain sequence of the α chain of the TCR molecule of the present disclosure may be "TRAC*01", and the constant domain sequence of the β chain of the TCR molecule may be "TRBC1*01" or "TRBC2*01". The position 53 of the amino acid sequence given in TRAC*01 of the IMGT is Arg, which is described herein as Arg53 of exon 1 of TRAC*01, and so on. Preferably, the amino acid sequence of the α chain of the TCR molecule of the present disclosure is SEQ ID NO: 3, and/or the amino acid sequence of the β chain is SEQ ID NO: 7.

Native TCR is a membrane protein and is stabilized through its transmembrane region. Just as immunoglobulins (antibodies) are used as antigen recognition molecules, the TCR can also be developed for diagnosis and treatment, and at this point, it is necessary to obtain a soluble TCR molecule. The soluble TCR molecule does not comprise its transmembrane region. The soluble TCR has a wide range of applications. It can not only be used to study the interaction between the TCR and the pMHC, but also be used as a diagnostic tool for detecting infection or as a marker of autoimmune diseases. Similarly, the soluble TCR can be used for delivering therapeutic agents (such as cytotoxic compounds or immunostimulating compounds) to cells presenting specific antigens. In addition, the soluble TCR can also bind to other molecules (such as anti-CD3 antibodies) to redirect T cells so that they target cells presenting specific antigens. The present disclosure also obtains a soluble TCR having specificity for the KRAS G12V antigen short peptide.

In order to obtain the soluble TCR, in one aspect, the TCR of the present disclosure may be a TCR in which an artificial disulfide bond is introduced between residues of its α and β and chain constant domains. Cysteine residues form an artificial interchain disulfide bond between the α and β chain constant domains of the TCR. Cysteine residues can replace other amino acid residues at suitable positions in a native TCR to form an artificial interchain disulfide bond. For example, the cysteine residue substituted for Thr48 of exon 1 of TRAC*01 and the cysteine residue substituted for Ser57 of exon 1 of TRBC1*01 or TRBC2*01 form a disulfide bond. Other sites where cysteine residues are introduced to form a disulfide bond may be: Thr45 of TRAC*01 exon 1 and Ser77 of TRBC1*01 or TRBC2*01 exon 1; Tyr10 of TRAC*01 exon 1 and Ser17 of TRBC1*01 or TRBC2*01 exon 1; Thr45 of TRAC*01 exon 1 and Asp59 of TRBC1*01 or TRBC2*01 exon 1; Ser15 of TRAC*01 exon 1 and Glu15 of TRBC1*01 or TRBC2*01 exon 1; Arg53 of TRAC*01 exon 1 and Ser54 of TRBC1*01 or TRBC2*01 exon 1; Pro89 of TRAC*01 exon 1 and Ala19 of TRBC1*01 or TRBC2*01 exon 1; and Tyr10 of TRAC*01 exon 1 and Glu20 of TRBC1*01 or TRBC2*01 exon 1. That is, cysteine residues replace any group of the above-mentioned sites in a and chain constant domains. A maximum of 50, or a maximum of 30, or a maximum of 15, or a maximum of 10, or a maximum of 8 or fewer amino acids may be truncated at one or more C-termini of the constant domain of the TCR of the present disclosure such that it does not comprise cysteine residues to achieve the purpose of deleting natural disulfide bonds, or the cysteine residues forming a natural disulfide bond can also be mutated to another amino acid for achieving the above purpose.

As described above, the TCR of the present disclosure may comprise an artificial disulfide bond introduced between residues of its α and β chain constant domains. It is to be noted that the introduced artificial disulfide bond as described above can be contained or not contained between the constant domains, and the TCR of the present disclosure may contain a TRAC constant domain sequence and a TRBC1 or TRBC2 constant domain sequence. The TRAC constant domain sequence and the TRBC1 or TRBC2 constant domain sequence of the TCR can be linked by a natural disulfide bond present in the TCR.

In order to obtain the soluble TCR, in another aspect, the TCR of the present disclosure also comprises a TCR having a mutation in its hydrophobic core region, and these mutations in hydrophobic core region are preferably mutations capable of increasing the stability of the TCR of the present disclosure, as described in the patent literature published as WO2014/206304. Such a TCR can have mutations at following positions in the variable domain hydrophobic core: (α and/or β chain) variable region amino acids at position 11, 13, 19, 21, 53, 76, 89, 91, 94, and/or α chain J gene (TRAJ) short peptide amino acids at reciprocal positions 3, 5, 7, and/or β chain J gene (TRBJ) short peptide amino acids at reciprocal positions 2, 4, 6, wherein the positions in an amino acid sequence are numbered according to the position numbers listed in the International Immunogenetics Information System (IMGT). Those skilled in the art will know the above International Immunogenetics Information System and can obtain the position numbers of the amino acid residues of different TCRs in the IMGT based on the database.

In the present disclosure, a TCR in which there is a mutation in the hydrophobic core region may be a stable single chain TCR consisting of TCR α and β chain variable domains that linked by a flexible peptide chain. It is to be noted that the flexible peptide chain in the present disclosure may be any peptide chain suitable for linking TCR α and β chain variable domains. For example, for the soluble single chain TCR constructed in Example 4 of the present disclosure, its α chain variable domain amino acid sequence is SEQ ID NO: 32 and the encoded nucleotide sequence is SEQ ID NO: 33; its β chain variable domain amino acid sequence of the TCR comprises SEQ ID NO: 34 and the encoded nucleotide sequence is SEQ ID NO: 35.

Additionally, as for stability, it was also disclosed in a patent literature 201680003540.2 that the introduction of an artificial interchain disulfide bond between the α chain variable region and the β chain constant region of a TCR can significantly improve the stability of the TCR. Therefore, an artificial interchain disulfide bond may be contained between the α chain variable region and the β chain constant region of the high-affinity TCR of the present disclosure. Specifically, cysteine residues forming an artificial interchain disulfide bond between the α chain variable region and the β chain constant region of the TCR are substituted for: an amino acid at position 46 of TRAV and an amino acid at position 60 of TRBC1*01 or TRBC2*01 exon 1; an amino acid at position 47 of TRAV and an amino acid at position 61 of TRBC1*01 or TRBC2*01 exon 1; an amino acid at position 46 of TRAV and an amino acid at position 61 of TRBC1*01 or TRBC2*01 exon 1; or an amino acid at position 47 of TRAV and an amino acid at position 60 of TRBC1*01 or TRBC2*01 exon 1. Preferably, the TCR comprises (i) all or part of the TCR α chain other than its transmembrane domain, and (ii) all or part of the TCR β chain other than its transmembrane domain, wherein both of (i) and (ii) comprise the variable domain and at least a portion of the constant domain of the TCR chain, and the α chain and the β chain form a heterodimer. More preferably, such a TCR may comprise an α chain variable domain, a β chain variable domain and all or part of a β chain constant domain other than the transmembrane domain, which, however, does not comprise an α chain constant domain, and the α chain variable domain of the TCR and the β chain form a heterodimer.

The TCR of the present disclosure can be provided in a form of multivalent complex. The multivalent TCR complex of the present disclosure comprises a polymer formed by combining two, three, four or more TCRs of the present disclosure, for example, a tetrameric domain of p53 can be used to produce a tetramer, or more TCRs of the present disclosure can be combined with another molecule to form a complex. The TCR complexes of the present disclosure can be used to track or target cells that present a particular antigen in vitro or in vivo, or produce intermediates of other multivalent TCR complexes with such uses.

The TCR of the present disclosure may be used alone or combined with a conjugate in a covalent manner or other manner, preferably in a covalent manner. The conjugate comprises a detectable label (for diagnostic purposes, wherein the TCR is used to detect the presence of a cell presenting a VVGAVGVGK-HLA A1101 or VVVGAVGVGK-HLA A1101 complex), a therapeutic agent, a PK (protein kinase) modifying moiety, or combination of any of the above described substances.

Detectable labels for diagnostic purposes comprise, but are not limited to, fluorescent or luminescent labels, radioactive labels, MRI (magnetic resonance imaging) or CT (electron computed X-Ray tomography technology) contrast agents, or enzymes capable of producing detectable products.

Therapeutic agents that can be combined with or coupled to the TCRs of the present disclosure comprise, but are not limited to: 1. Radionuclides (Koppe et al., 2005, Cancer metastasis reviews, 24, 539); 2. Biotoxin (Chaudhary et al., 1989, Nature, 339, 394; Epel et al., 2002, Cancer Immunology and Immunotherapy, 51, 565); 3. Cytokines, such as IL-2, etc. (Gillies et al., 1992, Proceedings of the National Academy of Sciences of the United States of America (PNAS), 89, 1428; Card et al., 2004, Cancer Immunology and Immunotherapy, 53, 345; Halin et al., 2003, Cancer Research, 63, 3202); 4. Antibody Fc fragment (Mosquera et al., 2005, The Journal of Immunology, 174, 4381); 5. Antibody scFv fragments (Zhu et al., 1995, International Journal of Cancer, 62, 319); 6. Gold nanoparticles/Nanorods (Lapotko et al., 2005, Cancer letters, 239, 36; Huang et al., 2006, Journal of the American Chemical Society, 128, 2115); 7. Viral particles (Peng et al., 2004, Gene therapy, 11, 1234); 8. Liposomes (Mamot et al., 2005, Cancer research, 65, 11631); 9. Nanomagnetic particles; 10. Prodrug activating enzymes (e.g., DT-diaphorase (DTD) or biphenyl hydrolase-like protein (BPHL); 11. chemotherapeutic agent (e.g., cisplatin) or any form of nanoparticles, and the like.

In addition, the TCR of the present disclosure may also be a hybrid TCR comprising sequences derived from more than one species. For example, studies have shown that the murine TCR can be expressed more effectively in human T cells than the human TCR. Therefore, the TCR of the present disclosure may comprise a human variable domain and a murine constant domain. The defect of this method is that it may trigger an immune response. Therefore, when it is used in the adoptive T cell therapy, there should be a regulatory solution for immunosuppression to allow the implantation of murine T cells.

It is to be understood that the amino acid names herein are represented by internationally accepted single English letters or three English letters, and the correspondence between the single English letters and the three English letters of an amino acid is: Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y), Val (V).

Nucleic Acid Molecule

In a second aspect of the present disclosure, a nucleic acid molecule encoding the TCR molecule of the first aspect of the present disclosure or part of the TCR molecule is provided, wherein the part of the TCR molecule may be one or more CDRs, α and/or β chain variable domains, and α and/or β chains.

The nucleotide sequences encoding the α chain CDRs of the TCR molecule of the first aspect of the present disclosure are as follows:

```
                                        (SEQ ID NO: 16)
α CDR1- gaccgagtttcccagtcc;

(SEQ ID NO: 17)
α CDR2- atatactccaatggtgac;
and (SEQ ID NO: 18)
α CDR3- gcctccctcaagggtaacaatgacatgcgc.
```

The nucleotide sequences encoding the β chain CDRs of the TCR molecule of the first aspect of the present disclosure are as follows:

```
                                           (SEQ ID NO: 19)
β CDR1- tcgggtcatgtatcc;

(SEQ ID NO: 20)
β CDR2- ttccagaatgaagctcaa;
and (SEQ ID NO: 21)
β CDR3- gccagcagctccagtaggtgggagcagcagttc.
```

Therefore, the nucleotide sequence of the nucleic acid molecule of the present disclosure encoding the TCRα chain of the present disclosure comprises SEQ ID NO: 16, SEQ ID NO: 17 and SEQ ID NO: 18, and/or the nucleotide sequence of the nucleic acid molecule of the present disclosure encoding the TCRβ chain of the present disclosure comprises SEQ ID NO: 19, SEQ ID NO: 20 and SEQ ID NO: 21.

The nucleotide sequence of the nucleic acid molecule of the present disclosure may be single-chain or double-chain, and the nucleic acid molecule may be RNA or DNA and may or may not contain introns. Preferably, the nucleotide sequence of the nucleic acid molecule of the present disclosure does not contain introns but is capable of encoding the polypeptide of the present disclosure. For example, the nucleotide sequence of the nucleic acid molecule of the present disclosure encoding the TCRα chain variable domain comprises SEQ ID NO: 2 and/or the nucleotide sequence of the nucleic acid molecule of the present disclosure encoding the TCRβ chain variable domain comprises SEQ ID NO: 6. Alternatively, the nucleotide sequence of the nucleic acid molecule of the present disclosure encoding the TCRα chain variable domain comprises SEQ ID NO: 33 and/or the nucleotide sequence of the nucleic acid molecule of the present disclosure encoding the TCRβ chain variable domain comprises SEQ ID NO: 35. More preferably, the nucleotide sequence of the nucleic acid molecule of the present disclosure comprises SEQ ID NO: 4 and/or SEQ ID NO: 8. Alternatively, the nucleotide sequence of the nucleic acid molecule of the present disclosure is SEQ ID NO: 31.

It is to be understood that due to the degeneracy of the genetic code, different nucleotide sequences may encode the same polypeptide. Therefore, a nucleic acid sequence encoding the TCR of the present disclosure may be the same as the nucleic acid sequence set forth in the Figures of the present disclosure or a degenerate variant thereof. By way of example, "degenerate variant", as used herein, refers to a nucleic acid sequence which encodes a protein with a sequence of SEQ ID NO: 1, but is different from the sequence of SEQ ID NO: 2.

The nucleotide sequence may be codon-optimized. Different cells are different in the use of specific codons. According to the type of cells, the codons in the sequence can be changed to increase the expression. Codon selection tables for mammalian cells as well as a variety of other organisms are well known to those skilled in the art.

The full length sequence of the nucleic acid molecule of the present disclosure or a fragment thereof can generally be obtained by, but not limited to, the PCR amplification method, the recombinant method or the synthetic method. At present, it has been possible to obtain a DNA sequence encoding the TCR (or a fragment thereof, or a derivative thereof) of the present disclosure completely by chemical synthesis. Then the DNA sequence can be introduced into various existing DNA molecules (or such as vectors) and cells known in the art. DNA can be a coding strand or a non-coding strand.

Vector

The present disclosure further relates to a vector comprising the nucleic acid molecule of the present disclosure, comprising an expression vector, that is, a construct capable of being expressed in vitro or in vivo. The common vector comprises bacterial plasmids, bacteriophages and animal and plant viruses.

The virus delivery system comprises, but is not limited to, adenovirus vectors, adeno-associated virus (AAV) vectors, herpesvirus vectors, retroviral vectors, lentivirus vectors, and baculovirus vectors.

Preferably, the vector can transfer the nucleotide of the present disclosure into a cell, such as in a T cell, such that the cell expresses a KRAS G12V antigen-specific TCR. Ideally, the vector should be capable of being continuously expressed at a high level in T cells.

Cell

The present disclosure further relates to a host cell genetically engineered using the vector or coding sequence of the present disclosure. The host cell comprises the vector of the present disclosure or has the exogenous nucleic acid molecule of the present disclosure integrated into its genome. The host cell is selected from prokaryotic cells and eukaryotic cells, e.g., *Escherichia coli*, yeast cells, CHO cells, and the like.

In addition, the present disclosure also comprises an isolated cell, particularly a T cell, which expresses the TCR of the present disclosure. The T cell may be derived from T cells isolated from a subject, or may be part of a mixed cell population isolated from the subject, such as a peripheral blood lymphocyte (PBL) population. For example, the cell may be isolated from peripheral blood mononuclear cells (PBMC) and may be a CD4$^+$ helper T cell or a CD8$^+$ cytotoxic T cell. The cell can be found in the mixed population of CD4$^+$ helper T cells/CD8$^+$ cytotoxic T cells. Generally, these cells may be activated with an antibody (e.g. an anti-CD3 or anti-CD28 antibody) to enable them to be more readily transfected. For example, these cells are transfected with the vector comprising the nucleic acid sequence encoding the TCR molecule of the present disclosure.

Alternatively, the cell of the present disclosure may also be or be derived from stem cells such as hematopoietic stem cells (HSC). The transferring of a gene to the HSC does not lead to TCR expression on the cell surface, because CD3 molecules are not expressed on the surface of stem cells. However, when a stem cell differentiates into a lymphoid precursor migrating to thymus, the expression of CD3 molecules will initiate the expression of the introduced TCR molecule on the surface of thymic cells.

There are a number of methods suitable for T cell transfection with DNA or RNA encoding the TCR of the present disclosure (e.g., Robbins et al., (2008) J. Immunol. 180: 6116-6131). T cells expressing the TCR of the present disclosure can be used in adoptive immunotherapy. Those skilled in the art can know many suitable methods for performing adoptive therapy (e.g., Rosenberg et al., (2008) Nat Rev Cancer 8(4): 299-308).

KRAS G12V Antigen-Related Disease

The present disclosure further relates to a method for treating and/or preventing a KRAS G12V-related disease in a subject, comprising the step of adoptively transferring KRAS G12V-specific T cells to a subject. The KRAS G12V-specific T cells can recognise a VVGAVGVGK-HLA A1101 or VVVGAVGVGK-HLA A1101 complex.

The KRAS G12V-specific T cell of the present disclosure can be used to treat any KRAS G12V-related diseases presenting the KRAS G12V antigen short peptide VVGAVGVGK-HLA A1101 or VVVGAVGVGK-HLA A1101 complex, comprising but not limited to tumors such as pancreatic cancer, lung cancer, colon cancer, rectal cancer, and the like.

The first 20 amino acid sequences of a wild-type KRAS protein without mutation are MTEYKLVVVG AGGVGK-SALT (SEQ ID NO: 39), and the amino acid at position 12 is G. VVGAGGVGK and VVVGAGGVGK correspond to positions 8-16 and 7-16 of the KRAS protein, respectively, and short peptides VVGAVGVGK and VVVGAVGVGK are formed after G12V mutation at these corresponding positions.

Therapeutic Method

Treatment can be performed by isolating T cells from a patient or a volunteer suffering from a KRAS G12V antigen-related disease, introducing the TCR of the present disclosure into the T cells, and then reinfusing these genetically engineered cells into the patient. Therefore, the present disclosure provides a method of treating a KRAS G12V-related disease, comprising infusing isolated T cells expressing the TCR of the present disclosure into a patient, preferably, the T cells are derived from the patient himself. Generally, the method comprises: (1) isolating T cells of a patient, (2) transducing the T cells in vitro with a nucleic acid molecule of the present disclosure or a nucleic acid molecule capable of encoding the TCR molecule of the present disclosure, and (3) infusing the genetically engineered T cells into the patient. The number of cells isolated, transfected and reinfused can be determined by the physician.

Main Advantages of the Present Disclosure:

(1) The TCR of the present disclosure can bind to the KRAS G12V antigen short peptide complex VVGAVGVGK-HLA A1101 or VVVGAVGVGK-HLA A1101, and the cell transduced with the TCR of the present disclosure can be specifically activated.

(2) The effector cell transduced with the TCR of the present disclosure has a good specific killing effect on the target cell.

The present disclosure is further illustrated by the following specific examples. It is to be understood that these examples are for illustrative purposes only and are not intended to limit the scope of the present disclosure. The experimental methods in the following examples which do not specify the specific conditions are usually performed under conventional conditions, for example, conditions described in Sambrook and Russell et al., *Molecular Cloning-A Laboratory Manual* (Third Edition) (2001) CSHL Publishing company, or in accordance with the conditions recommended by the manufacturer. Percentages and parts are by weight unless otherwise stated. Percentages and parts are by weight unless otherwise stated. All the experimental materials and reagents applied in the following examples are commercially available unless otherwise stated.

Example 1 Cloning of KRAS G12V Antigen Short Peptide Specific-T Cells

Peripheral blood lymphocytes (PBL) from a healthy volunteer with a genotype of HLA-A1101 were stimulated using a synthesized short peptide VVGAVGVGK (SEQ ID NO: 9) (Beijing Saibaisheng Gene Technology Co., Ltd.).

The short peptide was renatured with HLA-A1101 labeled with a biotin to prepare a pHLA haploid. These haploids were combined with a PE-labeled streptavidin (BD Company) to form a PE-labeled tetramer, and the tetramer and anti-CD8-APC double positive cells were sorted. The sorted cells were amplified, subjected to the secondary sorting according to the above method, and then monocloned using a limiting dilution method. Monoclonal cells were stained with a tetramer, and the screened double positive clones were shown in FIG. 3. The double positive clones obtained through layer-by-layer screening still needed to be subjected to further functional tests.

The function and specificity of the T cell colons were further detected by ELISPOT assay. Methods for detecting cellular function using ELISPOT assays are well known to those skilled in the art. In the IFN-γ ELISPOT assay of this example, effector cells used herein were the T cell clones obtained in the present disclosure, the target cells were LCLs cells loaded with the short peptides of the present disclosure, and the control groups were LCLs cells loaded with other short peptides and LCLs cells not loaded with short peptides.

Figure 14:
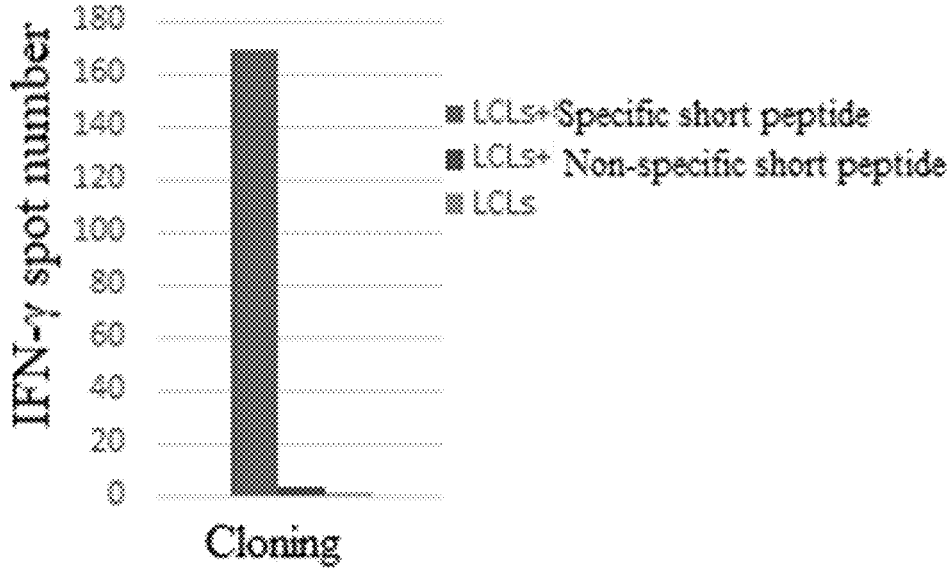
FIG. 14 shows obtained ELISPOT activation function verification results of T cell cloning.

Firstly, an ELISPOT plate was prepared. The steps of the ELISPOT assay were as follows: components of the assay were added to the ELISPOT plate: $2 \times 10^4$ LCLs cells/well and $2 \times 10^3$ T cell clones/well, 20 μL of specific short peptides were added to the experimental group, 20 μL of non-specific short peptides were added to the control group, 20 μL of culture medium (test medium) was added to the blank group was added with, in duplicate. The ELISPOT plate was incubated overnight ($37°$ C., 5% $CO_2$). The plate was washed, subjected to the secondary detection and color development, and dried for one hour, and the spots formed on the film were counted using an immunospot plate reader (ELISPOT READER system; AID20 company). Experimental results are shown in FIG. 14. The obtained T cell clones having specificity for a particular antigen exhibit significant specific response to LCLs cells loaded with short peptides of the present disclosure, but basically have no response to LCLs cells loaded with other unrelated peptides and LCLs cells not loaded with short peptides.

Example 2 Acquisition of TCR Genes of KRAS G12V Antigen Short Peptide-Specific T Cell Clones and Construction of Vectors The total RNA of the antigenic short peptide-specific, HLA-A1101-restricted T cell clones screened in Example 1 was extracted with Quick-RNA™ MiniPrep (ZYMO research). SMART RACE cDNA amplification kit of clontech was used to synthesize cDNA, and the primers were designed in the C-terminal conserved region of the human TCR gene. The sequence was cloned into a T vector (TA-KARA) for sequencing. It is to be noted that this sequence is a complement sequence and does not contain introns. Through sequencing, the structures of the α chain and chain sequences of the TCR expressed by the double positive clone are shown in FIGS. 1 and 2, respectively. FIGS. 1*a*, 1*b*, 1*c*, 1*d*, 1*e*, and 1*f* show a TCRα chain variable domain amino acid sequence, a TCRα chain variable domain nucleotide sequence, a TCRα chain amino acid sequence, a TCRα chain nucleotide sequence, a TCRα chain amino acid sequence having a leader sequence, and a TCRα chain nucleotide sequence having a leader sequence, respectively; and FIGS. 2*a*, 2*b*, 2*c*, 2*d*, 2*e*, and 2*f* show a TCRβ chain variable domain amino acid sequence, a TCRβ chain variable domain nucleotide sequence, a TCRβ chain amino acid sequence, a TCRβ chain nucleotide sequence, a TCRβ chain amino acid sequence having a leader sequence, and a TCRβ chain nucleotide sequence having a leader sequence, respectively.

After identification, the α chain comprises CDRs having the following amino acid sequences:

```
                                    (SEQ ID NO: 10)
        α CDR1-DRVSQS;

(SEQ ID NO: 11)
        α CDR2-IYSNGD;
        and (SEQ ID NO: 12)
        α CDR3- ASLKGNNDMR;
``` and
the β chain comprises CDRs having the following amino acid sequences:

```
                                    (SEQ ID NO: 13)
        β CDR1- SGHVS;

(SEQ ID NO: 14)
        β CDR2- FQNEAQ;
        and (SEQ ID NO: 15)
        β CDR3- ASSSSRWEQQF.
```

The full length genes of the TCR α and β chains were cloned into lentivirus expression vector pLenti (addgene) by overlapping PCR. Specifically, fragment TCR α-2A-TCR β was obtained through the connection of the full length gene of the TCR α chain and the full length gene of the TCR β chain by overlapping PCR. Plasmid pLenti-TRA-2A-TRB-IRES-NGFR was obtained by the ligation of the lentivirus expression vector and TCR α-2A-TCR β. As a control, lentivirus vector pLentie-eGFP expressing eGFP was also constructed. After that, the pseudovirus was packaged with 293T/17.

Example 3 Expression, Refolding and Purification
of the KRAS G12V Antigen Short Peptide-Specific
Soluble TCR In order to obtain the soluble TCR molecule, the α and β chains of the TCR molecule of the present disclosure can respectively comprise only their variable domains and part of their constant domains, and one cysteine residue was introduced into the constant domains of the α and β chains respectively to form an artificial interchain disulfide bond, in which the positions of the cysteine residues introduced are Thr48 of exon 1 of TRAC*01 and Ser57 of exon 1 of TRBC2*01, respectively. The amino acid sequence and nucleotide sequence of the α chain are shown in FIGS. 4a and 4b, respectively, and the amino acid sequence and nucleotide sequence of the β chain are shown in FIGS. 5a and 5b, respectively. According to standard methods described in *Molecular Cloning a Laboratory Manual* (3rd edition, Sambrook and Russell), sequences of the target gene of the TCR α and β chains are synthesized and inserted into an expression vector pET28a+ (Novagene), in which the upstream and downstream cloning sites are NcoI and NotI, respectively. The inserted fragment was sequenced to confirm that it was correct.

Expression vectors for TCR α and β chains were transformed into the expression bacteria BL21 (DE3) by chemical transformation, respectively. The bacteria were grown in LB medium and induced with a final concentration of 0.5 mM IPTG at $OD_{600}$=0.6. The inclusion bodies formed after the TCR α and β chains were expressed were extracted by BugBuster Mix (Novagene) and repeatedly washed with BugBuster solution. The inclusion bodies were finally dissolved in 6 M guanidine hydrochloride, 10 mM dithiothreitol (DTT), 10 mM ethylenediaminetetraacetic acid (EDTA) and 20 mM Tris (pH 8.1).

The dissolved TCR α and β chains were rapidly mixed in 5 M urea, 0.4 M arginine, 20 mM Tris (pH 8.1), 3.7 mM cystamine, and 6.6 mM β-mercapoethylamine (4° C.) at a mass ratio of 1:1, and the final concentration was 60 mg/mL. After mixing, the solution was dialyzed against 10 volumes of deionized water (4° C.), after 12 hours, deionized water was exchanged with a buffer (20 mM Tris, pH 8.0), and dialysis was continued for 12 hours at 4° C. After completion of the dialysis, the solution was filtered through a 0.45 μM filter and purified through an anion exchange column (HiTrap Q HP, 5 mL, GE Healthcare). The elution peak of the TCR containing successfully refolded α and β dimers was confirmed by SDS-PAGE gel. The TCR was then further purified by gel filtration chromatography (HiPrep 16/60, Sephacryl S-100 HR, GE Healthcare). The purity of the purified TCR was determined by SDS-PAGE to be greater than 90%, and the concentration thereof was determined by BCA method. The SDS-PAGE gel diagram of the soluble TCR obtained in the present disclosure is shown in FIGS. 6a and 6b.

Example 4 Generation of a KRAS G12V Antigen
Short Peptide-Specific Soluble Single Chain TCR A stable single chain TCR molecule was constructed by connecting the TCR α and β chain variable domains obtained in Example 2 by a flexible short peptide (linker) by a site-directed mutagenesis method according to a patent literature WO2014/206304. The amino acid sequence and nucleotide sequence of the single chain TCR molecule are shown in FIGS. 7a and 7b, respectively. The amino acid sequence and nucleotide sequence of the α chain variable domain are shown in FIGS. 8a and 8b, respectively; the amino acid sequence and nucleotide sequence of the β chain variable domain are shown in FIGS. 9a and 9b, respectively; and the amino acid sequence and nucleotide sequence of the linker sequence are shown in FIGS. 10a and 10b, respectively.

The target gene was digested with NcoI and NotI and ligated with a pET28a vector digested with NcoI and NotI. The ligation product was transformed into *E. coli* DH5a, plated on a kanamycin-containing LB plate, inverted and cultured at 37° C. overnight, and the positive clones were picked for PCR screening. Positive recombinants were sequenced to determine the correct sequence and the recombinant plasmid was extracted and transferred into *E. coli* BL21 (DE3) for expression.

Example 5 Expression, Renaturation and
Purification of the KRAS G12V Antigen Short
Peptide-Specific Soluble Single Chain TCR All of BL21(DE 3) colonies containing the recombinant plasmid pET28α-template chain prepared in Example 4 were inoculated into LB medium containing kanamycin, cultured at 37° C. until $OD_{600}$ was 0.6-0.8. IPTG was added to a final concentration of 0.5 mM, and cultured at 37° C. for another 4 hours. The cell pellets were harvested by centrifugation at 5000 rpm for 15 minutes, and the cell pellets were lysed with Bugbuster Master Mix (Merck). The inclusion bodies were recovered by centrifugation at 6000 rpm for 15 minutes, followed by washing with Bugbuster (Merck) to remove cell debris and membrane fraction. The inclusion bodies were collected by centrifugation at 6000 rpm for 15 minutes, and dissolved in a buffer (20 mM Tris-HCl pH 8.0, 0.8 M urea), and the insoluble matters were removed by high-speed centrifugation. The supernatant was quantitatively determined by BCA method, and then dispensed and stored at −80° C. until use.

To 5 mg of the dissolved single chain TCR inclusion body protein, 2.5 mL of buffer (6 M Gua-HCl, 50 mM Tris-HCl pH 8.1, 100 mM NaCl, 10 mM EDTA) was added, and then DTT was added to a final concentration of 10 mM and incubated at 37° C. for 30 minutes. The single chain TCR as treated above was added dropwise to 125 mL of refolding buffer (100 mM Tris-HCl pH 8.1, 0.4 M L-arginine, 5 M urea, 2 mM EDTA, 6.5 mM β-mercapthoethylamine, 1.87 mM Cystamine) with a syringe, and stirred at 4° C. for 10 minutes. Then the refolded solution was loaded into a cellulose membrane dialysis bag with a cut-off of 4 kDa, and the dialysis bag was placed in 1 L of pre-cooled water and stirred slowly at 4° C. overnight. After 17 hours, the dialysis liquid was changed to 1 L of pre-chilled buffer (20 mM Tris-HCl pH 8.0) and dialysis was continued for 8 hours at 4° C. The dialysis liquid was then replaced with the same fresh buffer and dialysis was continued overnight. After 17 hours, the sample was filtered through a 0.45 μm filter, vacuum degassed and purified through an anion exchange column (HiTrap Q HP, GE Healthcare) with a linear gradient elution of 0-1 M NaCl prepared with 20 mM Tris-HCl pH 8.0. The collected fractions were subjected to SDS-PAGE analysis, and the fractions containing the single chain TCR were concentrated and further purified by a gel filtration column (Superdex 75 10/300, GE Healthcare), and the target components were also subjected to SDS-PAGE analysis.

The eluted fractions for BIAcore analysis were further tested for purity using gel filtration. The conditions were as follows: chromatographic column Agilent Bio S EC-3 (300 A, φ7.8×300 mm), mobile phase 150 mM phosphate buffer, flow rate 0.5 mL/min, column temperature 25° C., and UV detection wavelength 214 nm.

The SDS-PAGE gel diagram of the soluble single chain TCR obtained in the present disclosure is shown in FIG. 11.

Example 6 Binding Characterization

BIAcore Analysis

The specific binding affinity of the soluble TCR molecule of the present disclosure for the VVGAVGVGK-HLA A1101 complex was detected in this example.

The binding activity of the TCR molecules prepared in Examples 3 and 5 to the VVGAVGVGK-HLA A1101 complex was detected using a BIAcore T200 real-time analysis system. The anti-streptavidin antibody (GenScript) was added to a coupling buffer (10 mM sodium acetate buffer, pH 4.77), and then the antibody was passed through a CMS chip pre-activated with EDC and NHS to immobilize the antibody on the surface of the chip. The unreacted activated surface was finally blocked with a solution of ethanolamine in hydrochloric acid to complete the coupling process at a coupling level of about 15,000 RU.

A low concentration of streptavidin flowed over the surface of the antibody-coated chip, then the VVGAVGVGK-HLA A1101 complex flowed through the detection channel with another channel being used as a reference channel, and 0.05 mM biotin flowed over the chip for 2 minutes at a flow rate of 10 μL/min, thereby blocking the remaining binding sites for streptavidin.

The preparation process for the above VVGAVGVGK-HLA A1101 complex is described as follows:

a. Purification 100 mL of *E. coli* liquid induced to express a heavy or light chain was collected and centrifuged at 8000 g for 10 min at 4° C., and the cells were washed once with 10 mL of PBS and then vigorously shaken in 5 mL of BugBuster Master Mix Extraction Reagents (Merck) for resuspending the cells. The suspension was rotated and incubated for 20 minutes at room temperature and then centrifuged at 6000 g for 15 min at 4° C. The supernatant was discarded to collect inclusion bodies.

The above inclusion bodies was resuspended in 5 mL of BugBuster Master Mix, rotated and incubated at room temperature for 5 minutes. 30 mL of 10 time-diluted Bug-Buster was added, mixed, and centrifuged at 6000 g for 15 minutes at 4° C. The supernatant was discarded, and 30 mL of 10 time-diluted BugBuster was added to resuspend the inclusion bodies, mixed, centrifuged at 6000 g for 15 minutes at 4° C., and repeated twice. 30 mL of 20 mM Tris-HCl pH 8.0 was added to resuspend the inclusion bodies, mixed, and centrifuged at 6000 g for 15 minutes at 4° C. Finally, inclusion bodies were dissolved in 20 mM Tris-HCl 8M urea, and the purity of inclusion bodies was determined by SDS-PAGE and the concentration was measured by BCA kit.

b. Refolding

The synthesized short peptide VVGAVGVGK (Beijing Saibaisheng Gene Technology Co., Ltd.) was dissolved in DMSO to a concentration of 20 mg/mL. Inclusion bodies of light chain and heavy chain were solubilized in 8 M urea, 20 mM Tris pH 8.0, 10 mM DTT, and further denatured by adding 3 M guanidine hydrochloride, 10 mM sodium acetate, and 10 mM EDTA before refolding. VVGAVGVGK peptide was added to a refolding buffer (0.4 M L-arginine, 100 mM Tris pH 8.3, 2 mM EDTA, 0.5 mM oxidized glutathione, 5 mM reduced glutathione, 0.2 mM PMSF, cooled to 4° C.) at 25 mg/L (final concentration). Then 20 mg/L of light chain and 90 mg/L of heavy chain (final concentration, heavy chain were added in three portions, 8 hours/portion) were successively added and refolded at 4° C. for at least 3 days to completion of refolding, and SDS-PAGE was used to confirm refolding.

c. Purification Upon Refolding

The refolding buffer was replaced with 10 volumes of 20 mM Tris pH 8.0 for dialysis, and the buffer was exchanged for at least twice to substantially reduce the ionic strength of the solution. After dialysis, the protein solution was filtered through a 0.45 μm cellulose acetate filter and loaded onto a HiTrap Q HP (GE, General Electric Company) anion exchange column (5 mL bed volume). The protein was eluted with a linear gradient of 0-400 mM NaCl prepared in 20 mM Tris pH 8.0 using Akta Purifier (GE, General Electric Company), and the pMHC was eluted at approximately 250 mM NaCl. All peak fractions were collected and the purity thereof was detected by SDS-PAGE.

d. Biotinylation

Purified pMHC molecules were concentrated with a Millipore ultrafiltration tube, while the buffer was replaced with 20 mM Tris pH 8.0, and then biotinylation reagents 0.05 M Bicine pH 8.3, 10 mM ATP, 10 mM MgOAc, 50 μM D-Biotin, 100 μg/mL BirA enzyme (GST-BirA) were added. The resulting mixture was incubated at room temperature overnight, and SDS-PAGE was used to detect the completion of biotinylation.

e. Purification of Biotinylated Complex

The biotinylated and labeled pMHC molecules were concentrated to 1 mL with a Millipore ultrafiltration tube. The biotinylated pMHC was purified by gel filtration chromatography using an Akta Purifier (GE, General Electric Company). 1 mL of concentrated biotinylated pMHC molecules was loaded on a HiPrep™ 16/60 5200 HR column (GE, General Electric Company) pre-equilibrated with filtered PBS and eluted with PBS at a flow rate of 1 mL/minute. The biotinylated pMHC molecules were eluted as a single peak at about 55 mL. The protein-containing fractions were combined and concentrated with a Millipore ultrafiltration tube. The concentration of the protein was determined by BCA method (Thermo), protease inhibitor cocktail (Roche) was added, and the biotinylated pMHC molecules were dispensed and stored at –80° C.

Figure 13:
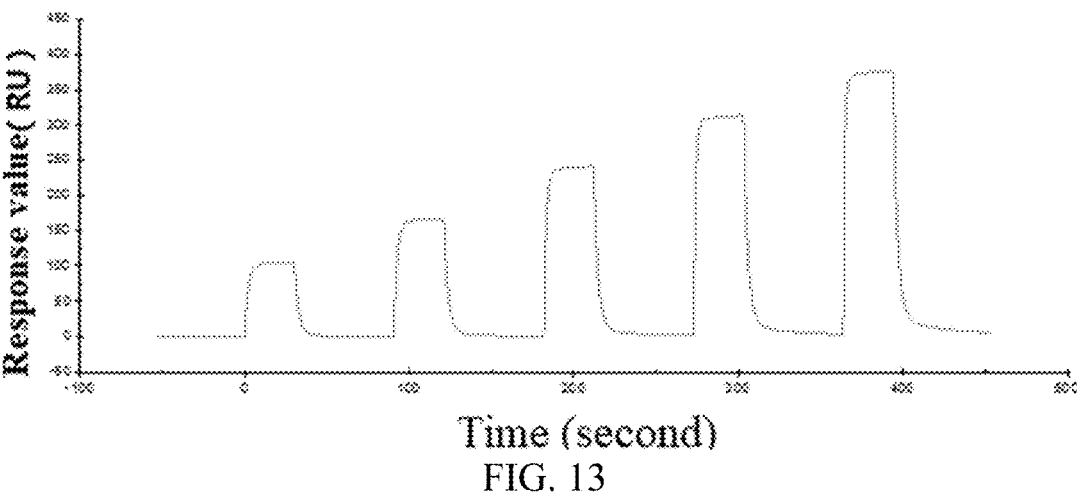
FIG. 13 is a BIAcore kinetic map of the binding of a soluble single chain TCR to a VVGAVGVGK-HLA A1101 complex in the present disclosure.

Kinetic parameters were calculated using BIAcore Evaluation software, and the kinetic maps of the binding of the soluble TCR molecule of the present disclosure and the soluble single chain TCR molecule constructed in the present disclosure to the VVGAVGVGK-HLA A1101 complex are shown in FIGS. 12 and 13, respectively. The maps show that both the soluble TCR molecule and the soluble single chain TCR molecule obtained in the present disclosure can bind to the VVGAVGVGK-HLA A1101 complex. Meanwhile, the above method is also used to detect the binding activity of the soluble TCR molecule of the present disclosure to other irrelevant antigenic short peptides and HLA complex, and the results show that the TCR molecule of the present disclosure does not bind to other irrelevant antigens.

Example 7 Activation Experiment of T Cells Transduced with the TCR of the Present Disclosure (with T2 as Target Cells)

Methods for detecting cellular functions using ELISPOT assays are well known to those skilled in the art. The IFN-γ production detected by ELISPOT assay was used as the readout of T cell activation to prove the specific activation reaction of the T cells transduced with the TCR of the present disclosure to the target cells.

Firstly, reagents were prepared, which comprise test medium: 10% FBS (Gibco, #16000-044) and RPMI 1640 (Gibco, #C11875500BT); washing buffer (PBST): 0.01 M PBS (Gibco, #C10010500BT)/0.05% Tween 20; a PVDF ELISPOT 96-well plate (Merck Millipore, #MSIPS4510); and a human IFN-γ ELISPOT PVDF-enzyme kit (BD) comprising all the other reagents required (capture and detection antibodies, streptavidin-alkaline phosphatase, and BCIP/NBT solution).

The target cells used in this experiment were T2 cells loaded with specific short peptides, T2 cells loaded with non-specific short peptides and T2 cells not loaded with short peptides. T2 cells were transfected with HLA-A1101. The specific short peptides were VVGAVGVGK (KRAS G12V, nonapeptide) and VVVGAVGVGK (KRAS G12V, decapeptide); and the non-specific peptides were VVGAGGVGK (KRAS short peptide without mutation), VVVGAGGVGK (KRAS short peptide without mutation), VVGADGVGK (KRAS G12D, KRAS short peptide with other mutations at position 12), VVVGADGVGK (KRAS G12D, KRAS short peptide with other mutations at position 12) and SSCSSCPLSK (other antigen short peptide).

The effector cells (T cells) used in this experiment were CD3+ T cells expressing the KRAS G12V antigen short peptide-specific TCR of the present disclosure, and CD3+ T cells from the same volunteer not transfected with the TCR of the present disclosure were used as the control group. T cells were stimulated with anti-CD3/CD28-coated beads (T cell amplimers, life technologies), transduced with lentivirus carrying the KRAS G12V antigen short peptide-specific TCR gene, amplified in 1640 medium containing 10% FBS containing 50 IU/mL IL-2 and 10 ng/mL IL-7 until day 9-12 after transduction, then placed in test medium, centrifuged at room temperature at 300 g for 10 minutes and washed. Then, the cells were resuspended in the test medium at 2× required final concentration. Negative control effector cells were also treated using the above method. Then, the corresponding short peptides were added to make the final concentration of short peptides in the ELISPOT well plate $10^{-6}$ M.

According to the instructions provided by the manufacturer, the well plate was prepared as follows: anti-human IFN-γ capture antibodies were diluted at 1:200 with 10 mL of sterile PBS per plate, and then 100 μL of diluted capture antibodies were equally added to each well. The well plate was incubated overnight at 4° C. After incubation, the well plate was washed to remove excess capture antibodies. RPMI 1640 medium containing 10% FBS was added at 100 μL/well, and the well plate was incubated at room temperature for 2 hours to block the well plate. The culture medium was then washed from the well plate and any residual washing buffer was removed by flicking and patting the ELISPOT well plate on the paper. Components of the assay were then added to the ELISPOT plate: $2 \times 10^4$ target cells/well and $1 \times 10^3$ effector cells/well (calculated according to the positive rate of transfection), and in duplicate.

The well plate was then incubated overnight (37° C./5% $CO_2$). On the second day, the culture medium was discarded, and the well plate was washed twice with double distilled water, and then washed three times with washing buffer, and patted on a paper towel to remove the residual washing buffer. The detection antibodies were then diluted with PBS containing 10% FBS diluted at 1:200, and added to each well at 100 μL/well. The well plate was incubated at room temperature for 2 hours, then washed with washing buffer three times, and patted on the paper towel to remove excessive washing buffer. Streptavidin-alkaline phosphatase was diluted with PBS containing 10% FBS at 1:100, 100 μL of diluted streptavidin-alkaline phosphatase was added to each well, and the well plate was incubated at room temperature for 1 hour, then washed with washing buffer four time, washed with PBSs twice, and patted on the paper towel to remove excessive washing buffer and PBS. After washing, BCIP/NBT solution provided by the kit was added at 100 μL/well for development. During development, the well plate was covered with tin foil, protected from light, and allowed to stand for 5 to 15 minutes. During this period, the spots on the developed well plate were routinely detected to determine the best time to terminate the reaction. The BCIP/NBT solution was removed, the well plate was rinsed with double distilled water to terminate the development reaction and spin-dried, then the bottom of the well plate was removed, the well plate was dried at room temperature until each well was completely dry, and the spots formed on the bottom film of the well plate were counted using an immunospot plate reader (CTL, Cellular Technology Limited).

The release of IFN-γ of the T cells transduced with the TCR of the present disclosure reacting to the target cells was detected by ELISPOT assay (as described above). The number of ELSPOT spots observed in each well was plotted by graphpad prism 6.

Figure 15:
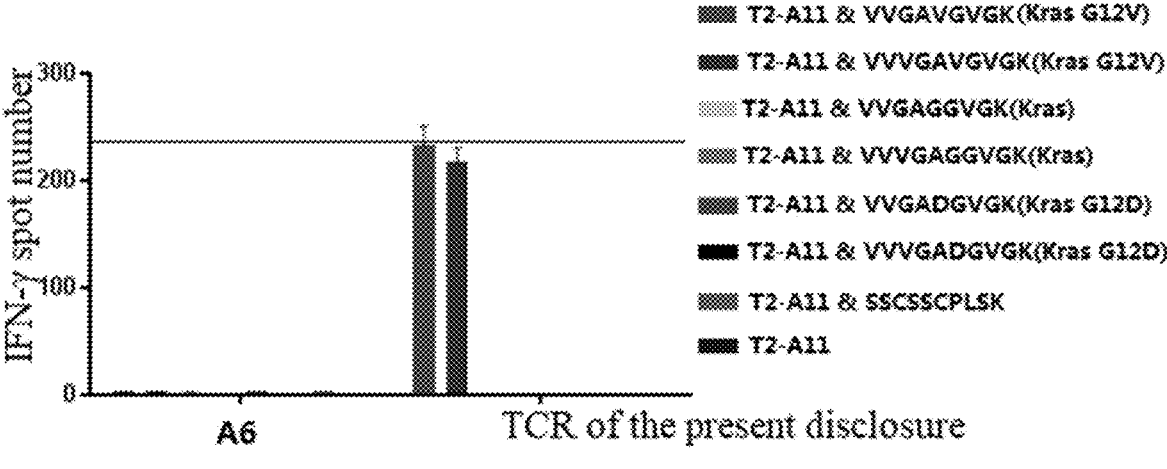
FIG. 15 is ELISPOT activation function verification results of effector cells transduced with the TCR of the present disclosure (with T2 as target cells).

Experimental results are shown in FIG. 15. T cells (effector cells) transduced with the TCR of the present disclosure have excellent activation response to target cells loaded with KRAS G12V (nonapeptide and decapeptide) and have no activation response to wild-type KRAS (nonapeptide and decapeptide) without mutation, KRAS G12D (nonapeptide and decapeptide) with other mutations at position 12, other antigen short peptides and unloaded target cells. It shows that the TCR of the present disclosure can specifically bind to KRAS G12V (nonapeptide and decapeptide) and produce cell activation reaction.

Example 8 Activation Experiment of T Cells Transduced with the TCR of the Present Disclosure (with Tumor Cell Lines as Target Cells)

This example also verifies that effector cells transfected with the TCR of the present disclosure have an excellent specific activation effect on target cells. The function and specificity of the high-affinity TCR of the present disclosure in cells were detected by ELISPOT assay.

Methods for detecting cellular functions using ELISPOT assays are well known to those skilled in the art. The effector cells (T cells) used herein were CD3+ T cells transfected with the KRAS G12V antigen short peptide-specific TCR of the present disclosure, and CD3+ T cells from the same volunteer not transfected with the TCR of the present disclosure were used as the control group. The target cell lines were A562-A11-TMG1 (over-expressed A11 and KRAS G12V), A562-A11 (over-expressed A11), A562-A11-TMG2 (over-expressed A11 and KRAS G12D), SK-MEL-1, SW620-A11 (over-expressed A11), and SW620 cells. The target cell lines A562-A11-TMG1 and SW620-A11 were used as positive tumor cell lines, and A562-A11, A562-A11-TMG2, SK-MEL-1 and SW620 were used as negative tumor cell lines as control.

Firstly, a ELISPOT plate was prepared. The ELISPOT plate was activated and coated with ethanol overnight at 4° C. On the first day of the experiment, the coating solution was removed, the plate was washed, blocked and incubated at room temperature for 2 hours, and the blocking solution was removed. Components of the assay were added to the ELISPOT plate: 2×10⁴ target cells/well and 10³ effector cells/well (calculated according to the positive rate of transfection) in duplicate. The plate was incubated overnight (37° C., 5% CO₂). On the second day of the experiment, the plate was washed, subjected to the secondary detection and development, and dried, and the spots formed on the film were counted using an immunospot plate reader (ELISPOT READER system; AID20 company).

Figure 16:
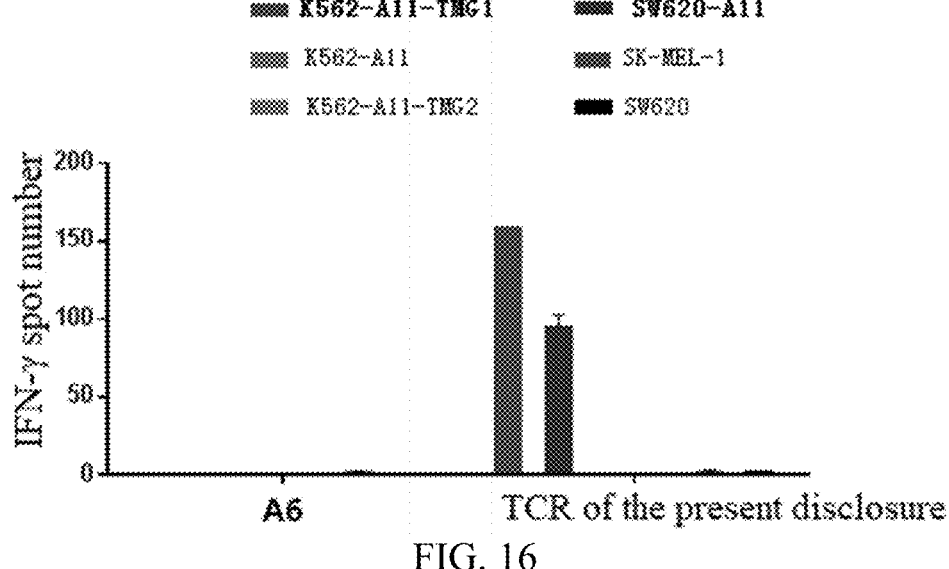
FIG. 16 is ELISPOT activation function verification results of effector cells transduced with the TCR of the present disclosure (with tumor cell lines as target cells).

Experimental results are shown in FIG. 16. The effector cells transfected with the TCR of the present disclosure exhibit excellent specific activation effects on positive target cell lines and have no response to negative target cell lines. In addition, the effector cells transfected with another TCR have no activation effect on the target cells.

Example 9 LDH Killing Function Assay of Effector Cells Transfected with the TCR of the Present Disclosure This example verifies the killing function of the cells transduced with the TCR of the present disclosure by measuring the release of LDH through a non-radioactive cytotoxicity assay. The assay is a colorimetric alternative to the 51Cr release cytotoxicity assay and quantifies lactate dehydrogenase (LDH) released after cell lysis. The LDH released in a culture medium was detected using a 30-minute coupled enzymatic reaction where the LDH converted a tetrazolium salt (INT) to red formazan. The amount of the red product produced was proportional to the number of cells lysed. Visible absorbance data at 490 nm can be collected using a standard 96-well plate reader.

Methods for detecting cellular functions using the release of LDH are well known to those skilled in the art. The effector cells (T cells) used herein were CD3+ T cells transfected with KRASTCR of the present disclosure, and CD3+ T cells from the same volunteer not transfected with the TCR of the present disclosure were used as the control group. The target cell lines were T2-A11 (over-expressed A11) of KRAS G12V (nonapeptide) VVGAVGVGK, T2-A11 (over-expressed A11), SK-MEL-28, SW620-A11 (over-expressed A11), SW620, and SW480-A11 (over-expressed A11) cells. T2-A11 loaded with VVGAVGVGK short peptides, SW620-A11 and SW480-A11 were used as positive tumor cell lines; and T2-A11, SK-MEL-28 and SW620 were used as negative tumor cell lines as control.

Firstly, an LDH plate was prepared. On the first day of the assay, components of the assay were added to the plate: 3×10⁴ target cell line cells/well and 3×10⁴ effector cells/well in triplicate. An effector cell spontaneous well, a target cell spontaneous well, a target cell maximum well, a volume correction control well and a culture medium background control well were set. The plate was incubated overnight (37° C., 5% CO₂). On the second day of the assay, the cells were subjected to detection and development. After the reaction was terminated, the absorbance at 450 nm was recorded with a microplate reader (Bioteck).

Figure 17:
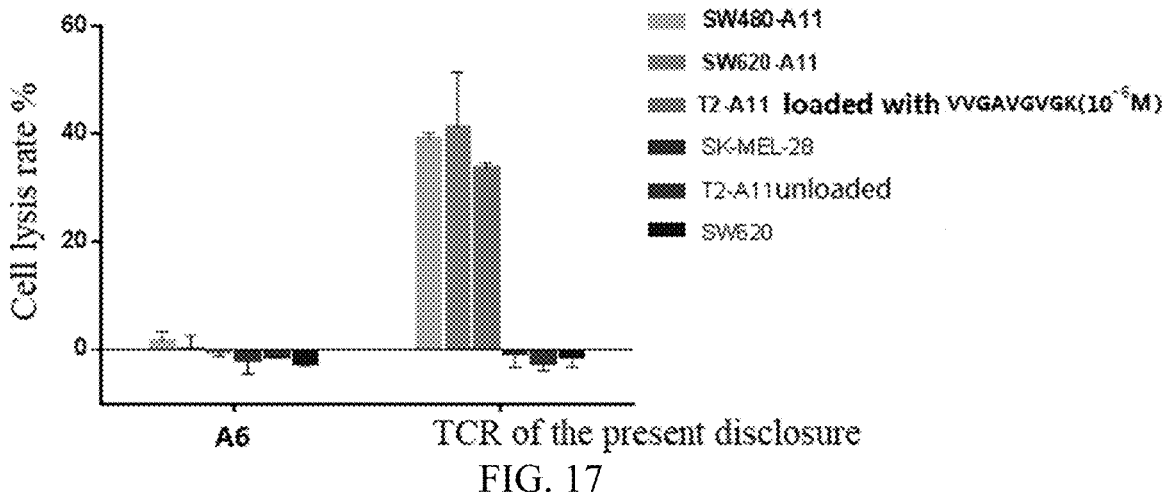
FIG. 17 is LDH killing function verification results of effector cells transduced with the TCR of the present disclosure.

Experimental results are shown in FIG. 17. The effector cells transfected with the TCR of the present disclosure exhibit strong killing effects on positive target cell lines and have no killing effect on negative target cell lines. In addition, the effector cells transfected with another TCR have no killing effect on the target cells.

All documents mentioned in the present disclosure are hereby incorporated by reference in their entireties, as if each is incorporated by reference. In addition, it is to be understood that after reading the teachings of the present disclosure, those skilled in the art can make various changes or modifications to the present disclosure, and these equivalent forms also fall within the scope as defined by the appended claims of the present application.

What is claimed is:

1. A T-cell receptor (TCR), wherein the TCR is capable of specifically binding to a VVGAVGVGK-HLA A1101 complex, the TCR comprises a TCRα chain variable domain and a TCRβ chain variable domain, wherein, the three complementarity determining regions (CDRs) of the TCRα chain variable domain are:

```
                              (SEQ ID NO: 10)
    α CDR1-DRVSQS;

(SEQ ID NO: 11)
    α CDR2-IYSNGD;
    and (SEQ ID NO: 12)
    α CDR3- ASLKGNNDMR;
    and
``` the three CDRs of the TCRβ chain variable domain are:

```
                              (SEQ ID NO: 13)
    β CDR1- SGHVS;

(SEQ ID NO: 14)
    β CDR2- FQNEAQ;
    and (SEQ ID NO: 15)
    β CDR3- ASSSSRWEQQF,
``` wherein cysteine residues form an artificial disulfide bond between the α and β chain constant domains of the TCR; and wherein the cysteine residues forming the artificial disulfide bond in the TCR are substituted for one or more groups of amino acids selected from the following:

Thr48 of TRAC*01 exon 1 and Ser57 of TRBC1*01 or TRBC2*01 exon 1;

Thr45 of TRAC*01 exon 1 and Ser77 of TRBC1*01 or TRBC2*01 exon 1;

Tyr10 of TRAC*01 exon 1 and Ser17 of TRBC1*01 or TRBC2*01 exon 1;

Thr45 of TRAC*01 exon 1 and Asp59 of TRBC1*01 or TRBC2*01 exon 1;

Ser15 of TRAC*01 exon 1 and Glu15 of TRBC1*01 or TRBC2*01 exon 1;

Arg53 of TRAC*01 exon 1 and Ser54 of TRBC1*01 or TRBC2*01 exon 1;

Pro89 of TRAC*01 exon 1 and Ala19 of TRBC1*01 or TRBC2*01 exon 1; and

Tyr10 of TRAC*01 exon 1 and Glu20 of TRBC1*01 or TRBC2*01 exon 1.

2. The TCR of claim 1, comprising a TCRα chain variable domain and a TCRβ chain variable domain, wherein the TCRα chain variable domain is an amino acid sequence having at least 90% sequence identity with SEQ ID NO: 1; and the TCRβ chain variable domain is an amino acid sequence having at least 90% sequence identity with SEQ ID NO: 5, provided that the three complementarity determining regions (CDRs) of the TCRα chain variable domain are:

```
                              (SEQ ID NO: 10)
    α CDR1-DRVSQS;

(SEQ ID NO: 11)
    α CDR2-IYSNGD;
    and (SEQ ID NO: 12)
    α CDR3- ASLKGNNDMR;
    and
``` the three CDRs of the TCRβ chain variable domain are:

```
                              (SEQ ID NO: 13)
    β CDR1- SGHVS;

(SEQ ID NO: 14)
    β CDR2- FQNEAQ;
    and (SEQ ID NO: 15)
    β CDR3- ASSSSRWEQQF.
```

3. The TCR of claim 1, wherein the TCR comprises an α chain variable domain amino acid sequence SEQ ID NO: 1; and, the TCR comprises a β chain variable domain amino acid sequence SEQ ID NO: 5.

4. The TCR of claim 1, wherein the α chain amino acid sequence of the TCR is SEQ ID NO: 3 and the β chain amino acid sequence of the TCR is SEQ ID NO: 7; or the α chain amino acid sequence of the TCR is SEQ ID NO: 26 and the β chain amino acid sequence of the TCR is SEQ ID NO: 28.

5. The TCR of claim 1, wherein the TCR is soluble; and the TCR is a single chain.

6. The TCR of claim 1, wherein the α chain variable domain amino acid sequence of the TCR comprises SEQ ID NO: 32 and the β chain variable domain amino acid sequence of the TCR comprises SEQ ID NO: 34.

7. The TCR of claim 1, wherein an anti-CD3 antibody is bound to the α chain and/or β chain of the TCR at C- or N-terminal.

8. A multivalent TCR complex, comprising at least two TCR molecules, wherein at least one TCR molecule is the TCR of claim 1.

9. A nucleic acid molecule, comprising a nucleic acid sequence encoding the TCR molecule of claim 1.

10. The nucleic acid molecule of claim 9, wherein the nucleic acid molecule comprises a nucleotide sequence SEQ ID NO: 4 encoding the TCRα chain and comprises a nucleotide sequence SEQ ID NO: 8 encoding the TCRβ chain.

11. The nucleic acid molecule of claim 9, wherein the nucleic acid molecule comprises a nucleotide sequence SEQ ID NO: 2 encoding the TCRα chain variable domain, and a nucleotide sequence SEQ ID NO: 6 encoding the TCRβ chain variable domain; or the nucleic acid molecule comprises a nucleotide sequence SEQ ID NO: 33 encoding the TCRα chain variable domain and a nucleotide sequence SEQ ID NO: 35 encoding the TCRβ chain variable domain.

12. A vector, comprising the nucleic acid molecule of claim 9.

13. An isolated host cell, having the nucleic acid molecule of claim 9 integrated into its genome or having a vector comprising the nucleic acid molecule of claim 9, wherein the nucleic acid molecule is exogenous with respect to the isolated host cell.

14. A pharmaceutical composition, comprising a pharmaceutically acceptable carrier, and the TCR of claim 1.

15. A pharmaceutical composition, comprising a pharmaceutically acceptable carrier and a cell, wherein the cell is transduced with the nucleic acid molecule of claim 9 or the cell is transduced with a vector comprising the nucleic acid molecule of claim 9.

16. A method for treating a disease, comprising administering an appropriate amount of the TCR of claim 1, wherein the disease is KRAS G12V-positive cancer.

17. The method of claim 16, wherein the disease is lung cancer, colorectal cancer, pancreatic cancer or gastric cancer.

18. A method for treating a disease, comprising administering an appropriate amount of a cell, wherein the cell is transduced with the nucleic acid molecule of claim 9 or the cell is transduced with a vector comprising the nucleic acid molecule of claim 9, wherein the disease is KRAS G12V-positive cancer.

19. The method of claim 18, wherein the disease is lung cancer, colorectal cancer, pancreatic cancer or gastric cancer.

\* \* \* \* \*

SEQUENCE LISTING

<160> NUMBER OF SEQ ID NOS: 39

<210> SEQ ID NO 1
<211> LENGTH: 110
<212> TYPE: PRT
<213> ORGANISM: Artificial sequence
<220> FEATURE:
<223> OTHER INFORMATION: Synthetic Polypeptide

<400> SEQUENCE: 1

```
Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Val Ser Gln Ser
                20                  25                  30

Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
        50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ser Leu Lys Gly Asn Asn
                85                  90                  95

Asp Met Arg Phe Gly Ala Gly Thr Arg Leu Thr Val Lys Pro
            100                 105                 110
```

<210> SEQ ID NO 2
<211> LENGTH: 330
<212> TYPE: DNA
<213> ORGANISM: Artificial sequence
<220> FEATURE:
<223> OTHER INFORMATION: Synthetic Polynucleotide

<400> SEQUENCE: 2

```
cagaaggagg tggagcagaa ttctggaccc ctcagtgttc cagagggagc cattgcctct      60
ctcaactgca cttacagtga ccgagtttcc cagtccttct tctggtacag acaatattct     120
gggaaaagcc ctgagttgat aatgtccata tactccaatg gtgacaaaga agatggaagg     180
tttacagcac agctcaataa agccagccag tatgtttctc tgctcatcag agactcccag     240
cccagtgatt cagccaccta cctctgtgcc tccctcaagg gtaacaatga catgcgcttt     300
ggagcaggga ccagactgac agtaaaacca                                      330
```

<210> SEQ ID NO 3
<211> LENGTH: 251
<212> TYPE: PRT
<213> ORGANISM: Artificial sequence
<220> FEATURE:
<223> OTHER INFORMATION: Synthetic Polypeptide

<400> SEQUENCE: 3

```
Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Val Ser Gln Ser
                20                  25                  30

Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
        50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ser Leu Lys Gly Asn Asn
                85                  90                  95

Asp Met Arg Phe Gly Ala Gly Thr Arg Leu Thr Val Lys Pro Asn Ile
            100                 105                 110

Gln Asn Pro Asp Pro Ala Val Tyr Gln Leu Arg Asp Ser Lys Ser Ser
            115                 120                 125
```

-continued

```
Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Thr Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
                180                 185                 190

Pro Glu Asp Thr Phe Phe Pro Ser Pro Glu Ser Ser Cys Asp Val Lys
                195                 200                 205

Leu Val Glu Lys Ser Phe Glu Thr Asp Thr Asn Leu Asn Phe Gln Asn
    210                 215                 220

Leu Ser Val Ile Gly Phe Arg Ile Leu Leu Leu Lys Val Ala Gly Phe
225                 230                 235                 240

Asn Leu Leu Met Thr Leu Arg Leu Trp Ser Ser
                245                 250

<210> SEQ ID NO 4
<211> LENGTH: 753
<212> TYPE: DNA
<213> ORGANISM: Artificial sequence
<220> FEATURE:
<223> OTHER INFORMATION: Synthetic Polynucleotide

<400> SEQUENCE: 4
cagaaggagg tggagcagaa ttctggaccc ctcagtgttc cagagggagc cattgcctct        60
ctcaactgca cttacagtga ccgagtttcc cagtccttct tctggtacag acaatattct       120
gggaaaagcc ctgagttgat aatgtccata tactccaatg gtgacaaaga agatggaagg       180
tttacagcac agctcaataa agccagccag tatgtttctc tgctcatcag agactcccag       240
cccagtgatt cagccaccta cctctgtgcc tccctcaagg gtaacaatga catgcgcttt       300
ggagcaggga ccagactgac agtaaaacca aatatccaga accctgaccc tgccgtgtac       360
cagctgagag actctaaatc cagtgacaag tctgtctgcc tattcaccga ttttgattct       420
caaacaaatg tgtcacaaag taaggattct gatgtgtata tcacagacaa aactgtgcta       480
gacatgaggt ctatggactt caagagcaac agtgctgtgg cctggagcaa caaatctgac       540
tttgcatgtg caaacgcctt caacaacagc attattccag aagacacctt cttccccagc       600
ccagaaagtt cctgtgatgt caagctggtc gagaaaagct ttgaaacaga tacgaaccta       660
aactttcaaa acctgtcagt gattgggttc cgaatcctcc tcctgaaagt ggccgggttt       720
aatctgctca tgacgctgcg gctgtggtcc agc                                    753

<210> SEQ ID NO 5
<211> LENGTH: 113
<212> TYPE: PRT
<213> ORGANISM: Artificial sequence
<220> FEATURE:
<223> OTHER INFORMATION: Synthetic Polypeptide

<400> SEQUENCE: 5

Gly Ala Gly Val Ser Gln Ser Pro Arg Tyr Lys Val Ala Lys Arg Gly
1                   5                   10                  15

Gln Asp Val Ala Leu Arg Cys Asp Pro Ile Ser Gly His Val Ser Leu
                20                  25                  30

Phe Trp Tyr Gln Gln Ala Leu Gly Gln Gly Pro Glu Phe Leu Thr Tyr
            35                  40                  45
```

-continued

```
Phe Gln Asn Glu Ala Gln Leu Asp Lys Ser Gly Leu Pro Ser Asp Arg
    50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Ser
                85                  90                  95

Ser Arg Trp Glu Gln Gln Phe Phe Gly Pro Gly Thr Arg Leu Thr Val
            100                 105                 110

Leu
```

```
<210> SEQ ID NO 6
<211> LENGTH: 339
<212> TYPE: DNA
<213> ORGANISM: Artificial sequence
<220> FEATURE:
<223> OTHER INFORMATION: Synthetic Polynucleotide

<400> SEQUENCE: 6
ggtgctggag tctcccagtc ccctaggtac aaagtcgcaa agagaggaca ggatgtagct      60
ctcaggtgtg atccaatttc gggtcatgta tccctttttt ggtaccaaca ggccctgggg     120
caggggccag agtttctgac ttatttccag aatgaagctc aactagacaa atcggggctg     180
cccagtgatc gcttctttgc agaaaggcct gagggatccg tctccactct gaagatccag     240
cgcacacagc aggaggactc cgccgtgtat ctctgtgcca gcagctccag taggtgggag     300
cagcagttct tcgggccagg gacacggctc accgtgcta                           339
```

```
<210> SEQ ID NO 7
<211> LENGTH: 292
<212> TYPE: PRT
<213> ORGANISM: Artificial sequence
<220> FEATURE:
<223> OTHER INFORMATION: Synthetic Polypeptide

<400> SEQUENCE: 7

Gly Ala Gly Val Ser Gln Ser Pro Arg Tyr Lys Val Ala Lys Arg Gly
1               5                   10                  15

Gln Asp Val Ala Leu Arg Cys Asp Pro Ile Ser Gly His Val Ser Leu
            20                  25                  30

Phe Trp Tyr Gln Gln Ala Leu Gly Gln Gly Pro Glu Phe Leu Thr Tyr
            35                  40                  45

Phe Gln Asn Glu Ala Gln Leu Asp Lys Ser Gly Leu Pro Ser Asp Arg
    50                  55                  60

Phe Phe Ala Glu Arg Pro Glu Gly Ser Val Ser Thr Leu Lys Ile Gln
65                  70                  75                  80

Arg Thr Gln Gln Glu Asp Ser Ala Val Tyr Leu Cys Ala Ser Ser Ser
                85                  90                  95

Ser Arg Trp Glu Gln Gln Phe Phe Gly Pro Gly Thr Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175
```

```
Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Glu Ser Tyr Gln Gln Gly Val Leu
            245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Ser Arg Gly
    290
```

<210> SEQ ID NO 8
<211> LENGTH: 876
<212> TYPE: DNA
<213> ORGANISM: Artificial sequence
<220> FEATURE:
<223> OTHER INFORMATION: Synthetic Polynucleotide

<400> SEQUENCE: 8

```
ggtgctggag tctcccagtc ccctaggtac aaagtcgcaa agagaggaca ggatgtagct      60
ctcaggtgtg atccaatttc gggtcatgta tccctttttt ggtaccaaca ggccctgggg     120
caggggccag agtttctgac ttatttccag aatgaagctc aactagacaa atcgggggctg    180 cccagtgatc gcttctttgc agaaaggcct gagggatccg tctccactct gaagatccag     240
cgcacacagc aggaggactc cgccgtgtat ctctgtgcca gcagctccag taggtgggag     300
cagcagttct tcgggccagg gacacggctc accgtgctag aggacctgaa aaacgtgttc     360
ccacccgagg tcgctgtgtt tgagccatca gaagcagaga tctcccacac ccaaaaggcc     420
acactggtgt gcctggccac aggcttctac cccgaccacg tggagctgag ctggtgggtg     480
aatgggaagg aggtgcacag tggggtcagc acagacccgc agcccctcaa ggagcagccc     540
gccctcaatg actccagata ctgcctgagc agccgcctga gggtctcggc caccttctgg     600 cagaacccc gcaaccactt ccgctgtcaa gtccagttct acgggctctc ggagaatgac      660
gagtggaccc aggatagggc caaacctgtc acccagatcg tcagcgccga ggcctggggt     720
agagcagact gtggcttcac ctccgagtct taccagcaag gggtcctgtc tgccaccatc     780
ctctatgaga tcttgctagg gaaggccacc ttgtatgccg tgctggtcag tgccctcgtg     840
ctgatggcca tggtcaagag aaaggattcc agaggc                               876
```

<210> SEQ ID NO 9
<211> LENGTH: 9
<212> TYPE: PRT
<213> ORGANISM: Artificial sequence
<220> FEATURE:
<223> OTHER INFORMATION: Synthetic Polypeptide

<400> SEQUENCE: 9

```
Val Val Gly Ala Val Gly Val Gly Lys
1               5
```

```
<210> SEQ ID NO 10
<211> LENGTH: 6
<212> TYPE: PRT
<213> ORGANISM: Artificial sequence
<220> FEATURE:
<223> OTHER INFORMATION: Synthetic Polypeptide

<400> SEQUENCE: 10

Asp Arg Val Ser Gln Ser
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic Polypeptide

<400> SEQUENCE: 11

Ile Tyr Ser Asn Gly Asp
1               5

<210> SEQ ID NO 12
<211> LENGTH: 10
<212> TYPE: PRT
<213> ORGANISM: Artificial sequence
<220> FEATURE:
<223> OTHER INFORMATION: Synthetic Polypeptide

<400> SEQUENCE: 12

Ala Ser Leu Lys Gly Asn Asn Asp Met Arg
1               5                   10

<210> SEQ ID NO 13
<211> LENGTH: 5
<212> TYPE: PRT
<213> ORGANISM: Artificial sequence
<220> FEATURE:
<223> OTHER INFORMATION: Synthetic Polypeptide

<400> SEQUENCE: 13

Ser Gly His Val Ser
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic Polypeptide

<400> SEQUENCE: 14

Phe Gln Asn Glu Ala Gln
1               5

<210> SEQ ID NO 15
<211> LENGTH: 11
<212> TYPE: PRT
<213> ORGANISM: Artificial sequence
<220> FEATURE:
<223> OTHER INFORMATION: Synthetic Polypeptide

<400> SEQUENCE: 15

Ala Ser Ser Ser Ser Arg Trp Glu Gln Gln Phe
1               5                   10

<210> SEQ ID NO 16
```

-continued

```
<211> LENGTH: 18
<212> TYPE: DNA
<213> ORGANISM: Artificial sequence
<220> FEATURE:
<223> OTHER INFORMATION: Synthetic Polynucleotide

<400> SEQUENCE: 16
gaccgagttt cccagtcc                                                    18

<210> SEQ ID NO 17
<211> LENGTH: 18
<212> TYPE: DNA
<213> ORGANISM: Artificial sequence
<220> FEATURE:
<223> OTHER INFORMATION: Synthetic Polynucleotide

<400> SEQUENCE: 17
atatactcca atggtgac                                                    18

<210> SEQ ID NO 18
<211> LENGTH: 30
<212> TYPE: DNA
<213> ORGANISM: Artificial sequence
<220> FEATURE:
<223> OTHER INFORMATION: Synthetic Polynucleotide

<400> SEQUENCE: 18
gcctccctca agggtaacaa tgacatgcgc                                       30

<210> SEQ ID NO 19
<211> LENGTH: 15
<212> TYPE: DNA
<213> ORGANISM: Artificial sequence
<220> FEATURE:
<223> OTHER INFORMATION: Synthetic Polynucleotide

<400> SEQUENCE: 19
tcgggtcatg tatcc                                                       15

<210> SEQ ID NO 20
<211> LENGTH: 18
<212> TYPE: DNA
<213> ORGANISM: Artificial sequence
<220> FEATURE:
<223> OTHER INFORMATION: Synthetic Polynucleotide

<400> SEQUENCE: 20
ttccagaatg aagctcaa                                                    18

<210> SEQ ID NO 21
<211> LENGTH: 33
<212> TYPE: DNA
<213> ORGANISM: Artificial sequence
<220> FEATURE:
<223> OTHER INFORMATION: Synthetic Polynucleotide

<400> SEQUENCE: 21
gccagcagct ccagtaggtg ggagcagcag ttc                                   33

<210> SEQ ID NO 22
<211> LENGTH: 272
<212> TYPE: PRT
<213> ORGANISM: Artificial sequence
<220> FEATURE:
<223> OTHER INFORMATION: Synthetic Polypeptide

<400> SEQUENCE: 22
```

-continued

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
            35                  40                  45

Arg Val Ser Gln Ser Phe Phe Trp Tyr Arg Gln Tyr Ser Gly Lys Ser
        50                  55                  60

Pro Glu Leu Ile Met Ser Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ser
                100                 105                 110

Leu Lys Gly Asn Asn Asp Met Arg Phe Gly Ala Gly Thr Arg Leu Thr
            115                 120                 125

Val Lys Pro Asn Ile Gln Asn Pro Asp Pro Ala Val Tyr Gln Leu Arg
        130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
                180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
        210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 23
<211> LENGTH: 816
<212> TYPE: DNA
<213> ORGANISM: Artificial sequence
<220> FEATURE:
<223> OTHER INFORMATION: Synthetic Polynucleotide

<400> SEQUENCE: 23
atgaaatcct tgagagtttt actagtgatc ctgtggcttc agttgagctg ggtttggagc      60
caacagaagg aggtggagca gaattctgga cccctcagtg ttccagaggg agccattgcc     120
tctctcaact gcacttacag tgaccgagtt tcccagtcct tcttctggta cagacaatat     180
tctgggaaaa gccctgagtt gataatgtcc atatactcca atggtgacaa agaagatgga     240
aggtttacag cacagctcaa taaagccagc cagtatgttt ctctgctcat cagagactcc     300
cagcccagtg attcagccac ctacctctgt gcctccctca gggtaacaa tgacatgcgc     360 tttggagcag ggaccagact gacagtaaaa ccaaatatcc agaaccctga ccctgccgtg     420
taccagctga gagactctaa atccagtgac aagtctgtct gcctattcac cgattttgat     480
tctcaaacaa atgtgtcaca aagtaaggat tctgatgtgt atatcacaga caaaactgtg     540

-continued

```
ctagacatga ggtctatgga cttcaagagc aacagtgctg tggcctggag caacaaatct      600
gactttgcat gtgcaaacgc cttcaacaac agcattattc cagaagacac cttcttcccc      660
agcccagaaa gttcctgtga tgtcaagctg gtcgagaaaa gctttgaaac agatacgaac      720
ctaaactttc aaaacctgtc agtgattggg ttccgaatcc tcctcctgaa agtggccggg      780
tttaatctgc tcatgacgct gcggctgtgg tccagc                              816
```

<210> SEQ ID NO 24
<211> LENGTH: 311
<212> TYPE: PRT
<213> ORGANISM: Artificial sequence
<220> FEATURE:
<223> OTHER INFORMATION: Synthetic Polypeptide

<400> SEQUENCE: 24

```
Met Gly Thr Arg Leu Leu Cys Trp Val Val Leu Gly Phe Leu Gly Thr
1               5                   10                  15

Asp His Thr Gly Ala Gly Val Ser Gln Ser Pro Arg Tyr Lys Val Ala
            20                  25                  30

Lys Arg Gly Gln Asp Val Ala Leu Arg Cys Asp Pro Ile Ser Gly His
        35                  40                  45

Val Ser Leu Phe Trp Tyr Gln Gln Ala Leu Gly Gln Gly Pro Glu Phe
    50                  55                  60

Leu Thr Tyr Phe Gln Asn Glu Ala Gln Leu Asp Lys Ser Gly Leu Pro
65                  70                  75                  80

Ser Asp Arg Phe Phe Ala Glu Arg Pro Glu Gly Ser Val Ser Thr Leu
                85                  90                  95

Lys Ile Gln Arg Thr Gln Gln Glu Asp Ser Ala Val Tyr Leu Cys Ala
            100                 105                 110

Ser Ser Ser Ser Arg Trp Glu Gln Gln Phe Phe Gly Pro Gly Thr Arg
        115                 120                 125

Leu Thr Val Leu Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
```

305                    310

<210> SEQ ID NO 25
<211> LENGTH: 933
<212> TYPE: DNA
<213> ORGANISM: Artificial sequence
<220> FEATURE:
<223> OTHER INFORMATION: Synthetic Polynucleotide

<400> SEQUENCE: 25
atgggcacca ggctcctctg ctgggtggtc ctgggtttcc tagggacaga tcacacaggt      60
gctggagtct cccagtcccc taggtacaaa gtcgcaaaga gaggacagga tgtagctctc     120
aggtgtgatc caatttcggg tcatgtatcc cttttttggt accaacaggc cctggggcag     180
gggccagagt ttctgactta tttccagaat gaagctcaac tagacaaatc ggggctgccc     240
agtgatcgct tctttgcaga aaggcctgag ggatccgtct ccactctgaa gatccagcgc     300
acacagcagg aggactccgc cgtgtatctc tgtgccagca gctccagtag gtgggagcag     360
cagttcttcg ggccagggac acggctcacc gtgctagagg acctgaaaaa cgtgttccca     420
cccgaggtcg ctgtgtttga gccatcagaa gcagagatct cccacaccca aaaggccaca     480
ctggtgtgcc tggccacagg cttctacccc gaccacgtgg agctgagctg gtgggtgaat     540
gggaaggagg tgcacagtgg ggtcagcaca gacccgcagc ccctcaagga gcagcccgcc     600
ctcaatgact ccagatactg cctgagcagc cgcctgaggg tctcggccac cttctggcag     660
aacccccgca accacttccg ctgtcaagtc cagttctacg ggctctcgga gaatgacgag     720
tggacccagg atagggccaa acctgtcacc cagatcgtca gcgccgaggc ctgggggtaga     780 gcagactgtg gcttcacctc cgagtcttac cagcaagggg tcctgtctgc caccatcctc     840
tatgagatct tgctagggaa ggccaccttg tatgccgtgc tggtcagtgc cctcgtgctg     900
atggccatgg tcaagagaaa ggattccaga ggc                                  933

<210> SEQ ID NO 26
<211> LENGTH: 205
<212> TYPE: PRT
<213> ORGANISM: Artificial sequence
<220> FEATURE:
<223> OTHER INFORMATION: Synthetic Polypeptide

<400> SEQUENCE: 26

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Val Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Ile Arg Asp Ser
65                  70                  75                  80

Gln Pro Ser Asp Ser Ala Thr Tyr Leu Cys Ala Ser Leu Lys Gly Asn
                85                  90                  95

Asn Asp Met Arg Phe Gly Ala Gly Thr Arg Leu Thr Val Lys Pro Asn
            100                 105                 110

Ile Gln Asn Pro Asp Pro Ala Val Tyr Gln Leu Arg Asp Ser Lys Ser
        115                 120                 125

Ser Asp Lys Ser Val Cys Leu Phe Thr Asp Phe Asp Ser Gln Thr Asn

```
            130                135                140

Val Ser Gln Ser Lys Asp Ser Asp Val Tyr Ile Thr Asp Lys Cys Val
145                150                155                160

Leu Asp Met Arg Ser Met Asp Phe Lys Ser Asn Ser Ala Val Ala Trp
                165                170                175

Ser Asn Lys Ser Asp Phe Ala Cys Ala Asn Ala Phe Asn Asn Ser Ile
            180                185                190

Ile Pro Glu Asp Thr Phe Phe Pro Ser Pro Glu Ser Ser
        195                200                205

<210> SEQ ID NO 27
<211> LENGTH: 618
<212> TYPE: DNA
<213> ORGANISM: Artificial sequence
<220> FEATURE:
<223> OTHER INFORMATION: Synthetic Polynucleotide

<400> SEQUENCE: 27
atgcagaaag aagtggaaca gaattctgga cccctcagtg ttccagaggg agccattgcc        60
tctctcaact gcacttacag tgaccgagtt tcccagtcct tcttctggta cagacaatat       120
tctgggaaaa gccctgagtt gataatgtcc atatactcca atggtgacaa agaagatgga       180
aggtttacag cacagctcaa taaagccagc cagtatgttt ctctgctcat cagagactcc       240
cagcccagtg attcagccac ctacctctgt gcctccctca agggtaacaa tgacatgcgc       300
tttggagcag ggaccagact gacagtaaaa ccaaatatcc agaaccctga ccctgccgtg       360
taccagctga gagactctaa gtcgagtgac aagtctgtct gcctattcac cgattttgat       420
tctcaaacaa atgtgtcaca agtaaggat tctgatgtgt atatcacaga caaatgtgtg       480
ctagacatga ggtctatgga cttcaagagc aacagtgctg tggcctggag caacaaatct       540
gactttgcat gtgcaaacgc cttcaacaac agcattattc cagaagacac cttcttcccc       600
agcccagaaa gttcctaa                                                     618

<210> SEQ ID NO 28
<211> LENGTH: 244
<212> TYPE: PRT
<213> ORGANISM: Artificial sequence
<220> FEATURE:
<223> OTHER INFORMATION: Synthetic Polypeptide

<400> SEQUENCE: 28

Met Gly Ala Gly Val Ser Gln Ser Pro Arg Tyr Lys Val Ala Lys Arg
1                5                10                15

Gly Gln Asp Val Ala Leu Arg Cys Asp Pro Ile Ser Gly His Val Ser
                20                25                30

Leu Phe Trp Tyr Gln Gln Ala Leu Gly Gln Gly Pro Glu Phe Leu Thr
            35                40                45

Tyr Phe Gln Asn Glu Ala Gln Leu Asp Lys Ser Gly Leu Pro Ser Asp
        50                55                60

Arg Phe Phe Ala Glu Arg Pro Glu Gly Ser Val Ser Thr Leu Lys Ile
65                70                75                80

Gln Arg Thr Gln Gln Glu Asp Ser Ala Val Tyr Leu Cys Ala Ser Ser
                85                90                95

Ser Ser Arg Trp Glu Gln Gln Phe Phe Gly Pro Gly Thr Arg Leu Thr
            100                105                110

Val Leu Glu Asp Leu Lys Asn Val Phe Pro Pro Glu Val Ala Val Phe
            115                120                125
```

```
Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Ala Leu Ser Ser
                180                 185                 190

Arg Leu Arg Val Ser Ala Thr Phe Trp Gln Asp Pro Arg Asn His Phe
            195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp
```

```
<210> SEQ ID NO 29
<211> LENGTH: 735
<212> TYPE: DNA
<213> ORGANISM: Artificial sequence
<220> FEATURE:
<223> OTHER INFORMATION: Synthetic Polynucleotide

<400> SEQUENCE: 29
atgggtgcag gtgttagcca gtcccctagg tacaaagtcg caaagagagg acaggatgta      60
gctctcaggt gtgatccaat ttcgggtcat gtatcccttt tttggtacca acaggccctg     120
gggcaggggc cagagtttct gacttatttc cagaatgaag ctcaactaga caaatcgggg     180
ctgcccagtg atcgcttctt tgcagaaagg cctgagggat ccgtctccac tctgaagatc     240
cagcgcacac agcaggagga ctccgccgtg tatctctgtg ccagcagctc cagtaggtgg     300
gagcagcagt tcttcgggcc agggacacgg ctcaccgtgc tagaggacct gaaaaacgtg     360
ttcccacccg aggtcgctgt gtttgagcca tcagaagcag agatctccca cacccaaaag     420
gccacactgg tgtgcctggc caccggtttc taccccgacc acgtggagct gagctggtgg     480
gtgaatggga aggaggtgca cagtggggtc tgcacagacc cgcagcccct caaggagcag     540
cccgccctca atgactccag atacgctctg agcagccgcc tgagggtctc ggccaccttc     600
tggcaggacc cccgcaacca cttccgctgt caagtccagt tctacgggct ctcggagaat     660
gacgagtgga cccaggatag ggccaaaccc gtcacccaga tcgtcagcgc cgaggcctgg     720
ggtagagcag actaa                                                      735
```

```
<210> SEQ ID NO 30
<211> LENGTH: 247
<212> TYPE: PRT
<213> ORGANISM: Artificial sequence
<220> FEATURE:
<223> OTHER INFORMATION: Synthetic Polypeptide

<400> SEQUENCE: 30

Gln Lys Glu Val Glu Gln Asn Ser Gly Pro Leu Ser Val Pro Glu Gly
1               5                   10                  15

Glu Asn Val Ser Ile Asn Cys Thr Tyr Ser Asp Arg Val Ser Gln Ser
                20                  25                  30

Phe Phe Trp Tyr Arg Gln Tyr Ser Gly Lys Ser Pro Glu Leu Ile Met
            35                  40                  45
```

```
Ser Ile Tyr Ser Asn Gly Asp Lys Glu Asp Gly Arg Phe Thr Ala Gln
    50              55              60

Leu Asn Lys Ala Ser Gln Tyr Val Ser Leu Glu Ile Arg Asp Val Gln
65              70              75              80

Pro Ser Asp Ser Ala Thr Tyr Leu Cys Ala Ser Leu Lys Gly Asn Asn
                85              90              95

Asp Met Arg Phe Gly Ala Gly Thr Arg Leu Thr Val Lys Pro Gly Gly
            100             105             110

Gly Ser Glu Gly Gly Gly Ser Glu Gly Gly Gly Ser Glu Gly Gly Gly
        115             120             125

Ser Glu Gly Gly Thr Gly Gly Ala Gly Val Ser Gln Ser Pro Arg Tyr
    130             135             140

Leu Ser Val Lys Arg Gly Gln Asp Val Thr Leu Arg Cys Asp Pro Ile
145             150             155             160

Ser Gly His Val Ser Leu Phe Trp Tyr Gln Gln Ala Pro Gly Gln Gly
                165             170             175

Pro Glu Phe Leu Thr Tyr Phe Gln Asn Glu Ala Gln Leu Asp Lys Ser
            180             185             190

Gly Leu Pro Ser Asp Arg Phe Asn Ala Glu Arg Pro Glu Gly Ser Val
        195             200             205

Ser Thr Leu Lys Ile Gln Arg Val Gln Pro Glu Asp Ser Ala Val Tyr
    210             215             220

Leu Cys Ala Ser Ser Ser Ser Arg Trp Glu Gln Gln Phe Phe Gly Pro
225             230             235             240

Gly Thr Arg Leu Thr Val Asp
            245
```

```
<210> SEQ ID NO 31
<211> LENGTH: 741
<212> TYPE: DNA
<213> ORGANISM: Artificial sequence
<220> FEATURE:
<223> OTHER INFORMATION: Synthetic Polynucleotide

<400> SEQUENCE: 31
cagaaagagg tggaacaaaa cagcggtccg ctgagcgtgc cggagggtga aaacgttagc      60
atcaactgca cctacagcga ccgtgttagc cagagcttct tttggtaccg tcaatatagc     120
ggtaaaagcc cggagctgat catgagcatt tatagcaacg gtgacaagga agatggccgt     180
ttcaccgcgc agctgaacaa agcgagccaa tacgtgagcc tggagattcg tgacgttcag     240
ccgagcgata gcgcgaccta tctgtgcgcg agcctgaagg gtaacaacga tatgcgtttt     300
ggtgcgggca cccgtctgac cgtgaaaccg ggtggcggta gcgagggcgg tggcagcgaa     360
ggtggcggta gcgagggcgg tggcagcgaa ggtggcaccg gtggcgcggg tgtgagccag     420
agcccgcgtt acctgagcgt gaagcgtggt caagacgtta ccctgcgttg cgatccgatc     480
agcggccacg ttagcctgtt ctggtatcag caagcgccgg gtcagggtcc ggagttcctg     540 acctatttctc agaacgaagc gcaactggac aagagcggtc tgccgagcga tcgttttaac     600
gcggagcgtc cggaaggcag cgtgagcacc ctgaaaattc agcgtgtgca accggaggac     660
agcgcggttt atctgtgcgc gagcagcagc agccgttggg aacagcaatt ctttggtccg     720
ggtacccgcc tgaccgttga t                                                741
```

```
<210> SEQ ID NO 32
<211> LENGTH: 110
<212> TYPE: PRT
```

```
<213> ORGANISM: Artificial sequence
<220> FEATURE:
<223> OTHER INFORMATION: Synthetic Polypeptide

<400> SEQUENCE: 32

Gln Lys Glu Val Glu Gln Asn Ser Gly Pro Leu Ser Val Pro Glu Gly
1               5                   10                  15

Glu Asn Val Ser Ile Asn Cys Thr Tyr Ser Asp Arg Val Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Glu Ile Arg Asp Val Gln
65                  70                  75                  80

Pro Ser Asp Ser Ala Thr Tyr Leu Cys Ala Ser Leu Lys Gly Asn Asn
                85                  90                  95

Asp Met Arg Phe Gly Ala Gly Thr Arg Leu Thr Val Lys Pro
            100                 105                 110

<210> SEQ ID NO 33
<211> LENGTH: 330
<212> TYPE: DNA
<213> ORGANISM: Artificial sequence
<220> FEATURE:
<223> OTHER INFORMATION: Synthetic Polynucleotide

<400> SEQUENCE: 33
cagaaagagg tggaacaaaa cagcggtccg ctgagcgtgc cggagggtga aaacgttagc          60
atcaactgca cctacagcga ccgtgttagc cagagcttct tttggtaccg tcaatatagc         120
ggtaaaagcc cggagctgat catgagcatt tatagcaacg gtgacaagga agatggccgt         180
ttcaccgcgc agctgaacaa agcgagccaa tacgtgagcc tggagattcg tgacgttcag         240
ccgagcgata gcgcgaccta tctgtgcgcg agcctgaagg gtaacaacga tatgcgtttt         300
ggtgcgggca cccgtctgac cgtgaaaccg                                          330

<210> SEQ ID NO 34
<211> LENGTH: 113
<212> TYPE: PRT
<213> ORGANISM: Artificial sequence
<220> FEATURE:
<223> OTHER INFORMATION: Synthetic Polypeptide

<400> SEQUENCE: 34

Gly Ala Gly Val Ser Gln Ser Pro Arg Tyr Leu Ser Val Lys Arg Gly
1               5                   10                  15

Gln Asp Val Thr Leu Arg Cys Asp Pro Ile Ser Gly His Val Ser Leu
            20                  25                  30

Phe Trp Tyr Gln Gln Ala Pro Gly Gln Gly Pro Glu Phe Leu Thr Tyr
        35                  40                  45

Phe Gln Asn Glu Ala Gln Leu Asp Lys Ser Gly Leu Pro Ser Asp Arg
    50                  55                  60

Phe Asn Ala Glu Arg Pro Glu Gly Ser Val Ser Thr Leu Lys Ile Gln
65                  70                  75                  80

Arg Val Gln Pro Glu Asp Ser Ala Val Tyr Leu Cys Ala Ser Ser Ser
                85                  90                  95

Ser Arg Trp Glu Gln Gln Phe Phe Gly Pro Gly Thr Arg Leu Thr Val
            100                 105                 110
```

-continued

Asp

<210> SEQ ID NO 35
<211> LENGTH: 339
<212> TYPE: DNA
<213> ORGANISM: Artificial sequence
<220> FEATURE:
<223> OTHER INFORMATION: Synthetic Polynucleotide

<400> SEQUENCE: 35
ggcgcgggtg tgagccagag cccgcgttac ctgagcgtga agcgtggtca agacgttacc      60
ctgcgttgcg atccgatcag cggccacgtt agcctgttct ggtatcagca agcgccgggt     120
cagggtccgg agttcctgac ctattttcag aacgaagcgc aactggacaa gagcggtctg     180
ccgagcgatc gttttaacgc ggagcgtccg gaaggcagcg tgagcaccct gaaaattcag     240
cgtgtgcaac cggaggacag cgcggtttat ctgtgcgcga gcagcagcag ccgttgggaa     300
cagcaattct ttggtccggg tacccgcctg accgttgat                            339

<210> SEQ ID NO 36
<211> LENGTH: 24
<212> TYPE: PRT
<213> ORGANISM: Artificial sequence
<220> FEATURE:
<223> OTHER INFORMATION: Synthetic Polypeptide

<400> SEQUENCE: 36

Gly Gly Gly Ser Glu Gly Gly Gly Ser Glu Gly Gly Gly Ser Glu Gly
1               5                   10                  15

Gly Gly Ser Glu Gly Gly Thr Gly
            20

<210> SEQ ID NO 37
<211> LENGTH: 72
<212> TYPE: DNA
<213> ORGANISM: Artificial sequence
<220> FEATURE:
<223> OTHER INFORMATION: Synthetic Polynucleotide

<400> SEQUENCE: 37
ggtggcggta gcgagggcgg tggcagcgaa ggtggcggta gcgagggcgg tggcagcgaa      60
ggtggcaccg gt                                                          72

<210> SEQ ID NO 38
<211> LENGTH: 10
<212> TYPE: PRT
<213> ORGANISM: Artificial sequence
<220> FEATURE:
<223> OTHER INFORMATION: Synthetic Polypeptide

<400> SEQUENCE: 38

Val Val Val Gly Ala Val Gly Val Gly Lys
1               5                   10

<210> SEQ ID NO 39
<211> LENGTH: 20
<212> TYPE: PRT

-continued

```
<213> ORGANISM: Artificial sequence
<220> FEATURE:
<223> OTHER INFORMATION: Synthetic Polypeptide

<400> SEQUENCE: 39

Met Thr Glu Tyr Lys Leu Val Val Val Gly Ala Gly Gly Val Gly Lys
1               5                   10                  15

Ser Ala Leu Thr
            20
```